(12) United States Patent
Yamashita

(10) Patent No.: US 7,655,904 B2
(45) Date of Patent: *Feb. 2, 2010

(54) TARGET WORKPIECE INSPECTION APPARATUS, IMAGE ALIGNMENT METHOD, AND COMPUTER-READABLE RECORDING MEDIUM WITH PROGRAM RECORDED THEREON

(75) Inventor: Kyoji Yamashita, Kanagawa (JP)

(73) Assignee: Advanced Mask Inspection Technology Inc., Yokohama-shi (JP)

( * ) Notice: Subject to any disclaimer, the term of this patent is extended or adjusted under 35 U.S.C. 154(b) by 396 days.

This patent is subject to a terminal disclaimer.

(21) Appl. No.: 11/678,748

(22) Filed: Feb. 26, 2007

(65) Prior Publication Data

US 2008/0036899 A1   Feb. 14, 2008

(30) Foreign Application Priority Data

Aug. 10, 2006   (JP)   ............................. 2006-217671

(51) Int. Cl.
*G01K 9/00*   (2006.01)

(52) U.S. Cl. ..................... 250/306; 250/307; 250/492.2; 250/492.22; 382/145; 382/151; 438/14; 348/340

(58) Field of Classification Search ................. 250/306, 250/307, 492.2, 492.22; 382/145, 151; 438/14
See application file for complete search history.

(56) References Cited

U.S. PATENT DOCUMENTS

2007/0053582 A1* 3/2007 Yamashita .................. 382/151
2007/0230770 A1* 10/2007 Kulkarni et al. ............. 382/149
2008/0037860 A1* 2/2008 Yamashita .................. 382/149
2008/0260234 A1* 10/2008 Yamashita .................. 382/144

FOREIGN PATENT DOCUMENTS

| JP | 63-88682 | 4/1988 |
|---|---|---|
| JP | 3-278057 | 12/1991 |
| JP | 5-281154 | 10/1993 |
| JP | 6-307826 | 11/1994 |

(Continued)

OTHER PUBLICATIONS

M. Takagi, et al., "Handbook on Image Analysis", University of Tokyo Press, 1991, 3 pages.

*Primary Examiner*—Nikita Wells
(74) *Attorney, Agent, or Firm*—Oblon, Spivak, McClelland, Maier & Neustadt, L.L.P.

(57) ABSTRACT

A target workpiece inspection apparatus comprises an optical image acquiring unit to acquire an optical image of a target workpiece, a reference image generating unit to generate a reference image to be compared, a difference judging unit to judge whether an absolute value of difference between pixel values of the images in each pixel at a preliminary alignment position between the images is smaller than a threshold value, a least-squares method displacement calculating unit to calculate a displacement amount displaced from the preliminary alignment position, by using a regular matrix for a least-squares method obtained from a result judged, a position correcting unit to correct an alignment position between the optical image and the reference image to a position displaced from the preliminary alignment position by the displacement amount, and a comparing unit to compare the optical image and the reference image whose alignment position has been corrected.

19 Claims, 15 Drawing Sheets

FOREIGN PATENT DOCUMENTS

| | | |
|---|---|---|
| JP | 8-64511 | 3/1996 |
| JP | 8-76359 | 3/1996 |
| JP | 8-77357 | 3/1996 |
| JP | 8-304997 | 11/1996 |
| JP | 10-96613 | 4/1998 |
| JP | 10-318950 | 12/1998 |
| JP | 11-132959 | 5/1999 |
| JP | 11-153550 | 6/1999 |
| JP | 2000-348177 | 12/2000 |
| JP | 2001-141677 | 5/2001 |
| JP | 2002-14062 | 1/2002 |
| JP | 2004-317427 | 11/2004 |

* cited by examiner

TARGET WORKPIECE INSPECTION APPARATUS, IMAGE ALIGNMENT METHOD, AND COMPUTER-READABLE RECORDING MEDIUM WITH PROGRAM RECORDED THEREON

CROSS-REFERENCE TO RELATED APPLICATION

This application is based upon and claims the benefit of priority from the prior Japanese Patent Application No. 2006-217671 filed on Aug. 10, 2006 in Japan, the entire contents of which are incorporated herein by reference.

BACKGROUND OF THE INVENTION

1. Field of the Invention

The present invention relates to a target workpiece or "sample" inspection apparatus, an image alignment method, or a program for causing a computer execute the method. For example, it is related with a pattern inspection technique which inspects a pattern defect of an object serving as a target workpiece used in manufacturing semiconductors, and an apparatus which inspects a defect of an ultrafine pattern of a photomask, a wafer, or a liquid crystal substrate used in manufacturing a semiconductor device or a liquid crystal display (LCD).

2. Related Art

In recent years, with an increase in high integration and large volume of large-scale integrated circuits (LSI), circuit line widths required for semiconductor devices are becoming narrower and narrower. These semiconductor devices are manufactured by exposing and transferring a pattern onto a wafer by means of a reduced-magnification projection exposure apparatus (a stepper) while using a master pattern (called a mask or a reticle, and will be generally called a mask hereinafter) on which a circuit pattern is written, "drawn" or "formed". Therefore, a pattern writing apparatus which can write fine circuits is used in manufacturing a mask for transferring fine circuit patterns onto a wafer. A pattern circuit may be directly written onto a wafer by using the pattern writing apparatus. In addition to a writing apparatus using electron beams, a laser beam pattern writing apparatus which uses laser beams to write a pattern is also developed.

An improvement in yield is crucial in manufacturing an LSI which requires a lot of manufacturing cost. However, as typified by one-gigabit class DRAM (Random Access Memory), the precision of a pattern which constitutes an LSI has been changing from sub-microns to nanometers. One of major factors which decrease the yield is pattern defects of a mask pattern used in exposing and transferring an ultrafine pattern onto a semiconductor wafer by a photolithography technique. In recent years, with miniaturization of an LSI pattern written on a semiconductor wafer, dimensions which have to be detected as a pattern defect are becoming extremely small. Therefore, a pattern inspection apparatus which inspects defects of a transfer mask used in manufacturing an LSI needs to be highly precise.

On the other hand, with development of multimedia, the size of a liquid crystal substrate of an LCD (Liquid Crystal Display) is becoming large: 500 mm×600 mm or more, and miniaturization of a pattern of a thin film transistor (TFT) or the like formed on a liquid crystal substrate is advancing. Therefore, it is increasingly required that a considerably small pattern defect should be inspected in a large area. For this reason, development of a target workpiece inspection apparatus which efficiently inspects a defect of a pattern of a large-area LCD and a photomask used in manufacturing the large-area LCD in a short time is urgently required.

As to a conventional pattern inspection apparatus, it is well-known that an inspection is performed by comparing an optical image captured by photographing a pattern written on a target workpiece, such as a lithography mask, at a predetermined magnification by using a magnifying optical system with design data or an optical image captured by photographing the same pattern on the target workpiece (see JP-A-08-76359, for example).

For example, the following is known as pattern inspection methods: "die to die inspection" which compares optical image data obtained by capturing the same patterns at different positions on the same mask, and "die to database inspection" which inputs drawing data (design pattern data) obtained by converting CAD data into appropriate format to be inputted by a drawing apparatus when drawing a pattern on a mask, into an inspection apparatus, generates design image data (reference image) based on the inputted drawing data, and compares the generated design image data with an optical image serving as measurement data obtained by capturing an image of the pattern. In these inspecting methods of the inspection apparatus, a target workpiece is placed on a stage to be scanned by a flux of light when the stage moves to perform inspection. The target workpiece is irradiated with flux of light from a light source and an illumination optical system. Light transmitted through the target workpiece or reflected by the target workpiece is focused onto a sensor through an optical system. The image captured by the sensor is transmitted to a comparing circuit as measurement data. In the comparing circuit, after alignment of the images, the measurement data is compared with reference data based on appropriate algorithm. When the measurement data is different from the reference data, it is judged there to be a pattern defect.

Herein, the reference image and the optical image are compared in each area of a predetermined size. Highly precise alignment between the reference image and the optical image is required for performing this comparison. A technique for calculating displacement amount or "deviation" between a reference image and an optical image by use of a least-squares method is disclosed in a reference (for example, refer to JP-A-11-153550). Further, an interpolation method for interpolating image data to be obtained by use of neighboring 4-point or 16-point image data is described in a reference (for example, refer to Image Analysis Handbook, pp. 442 to 443, University of Tokyo Press, first edition issued on Jan. 17, 1991).

With a miniaturization of a pattern, there is a demand for a further precision of alignment required for detecting ultrafine defects. However, in performing positional alignment by using a least-squares method calculation etc., if a pixel having a large defect exists, there is a problem that excessive alignment is performed because of being affected by a value of the pixel having the large defect. Consequently, it becomes difficult to execute highly precise alignment. The point herein is to correct only systematic error factors such as a stage placement error, a speed error or a magnification error, but not to correct inconsistent portions that occur locally and randomly such as defects, if possible.

As described above, highly precise alignment between a reference image and an optical image is required for performing comparison. However, with a miniaturization of a pattern, it has become difficult to detect relative displacement between the reference image and the optical image in high precision.

BRIEF SUMMARY OF THE INVENTION

It is an object of the present invention to provide a method and an apparatus which perform highly precise positional alignment between a reference image and an optical image.

In accordance with one aspect of the present invention, a target workpiece inspection apparatus includes an optical image acquiring unit configured to acquire an optical image of a target workpiece to be inspected on which a pattern is formed, a reference image generating unit configured to generate a reference image to be compared with the optical image, a difference judging unit configured to judge whether an absolute value of difference between a pixel value of the optical image and a pixel value of the reference image in each pixel at a preliminary alignment position between the optical image and the reference image is smaller than a predetermined threshold value, a least-squares method displacement calculating unit configured to calculate a displacement amount displaced from the preliminary alignment position, by using a regular matrix for a least-squares method obtained from a result judged by the difference judging unit, a position correcting unit configured to correct an alignment position between the optical image and the reference image to a position displaced from the preliminary alignment position by the displacement amount, and a comparing unit configured to compare the optical image and the reference image whose alignment position has been corrected.

In accordance with another aspect of the present invention, a target workpiece inspection apparatus includes an optical image acquiring unit configured to acquire an optical image of a target workpiece to be inspected on which a pattern is formed, a reference image generating unit configured to generate a reference image to be compared with the optical image, a difference judging unit configured to judge whether an absolute value of difference between a pixel value of the optical image and a pixel value of the reference image in each pixel at a preliminary alignment position between the optical image and the reference image is smaller than a predetermined threshold value, a first SSD (Sum of Squared Difference) calculating unit configured to calculate a first displacement amount from the preliminary alignment position between the optical image and the reference image to a first position where an SSD between the pixel value of the optical image and the pixel value of the reference image is minimized, a least-squares method displacement calculating unit configured to calculate a second displacement amount displaced from the preliminary alignment position, by using a regular matrix for a least-squares method obtained from a result determined by the difference judging unit, a second SSD calculating unit configured to calculate an SSD between the pixel value of the optical image and the pixel value of the reference image at a second position displaced from the preliminary alignment position by the second displacement amount, an SSD judging unit configured to judge which of the SSD at the first position and the SSD at the second position is smaller, a position correcting unit to correct an alignment position between the optical image and the reference image to a position where a smaller SSD as a result determined by the SSD judging unit is obtained, and a comparing unit configured to compare the optical image and the reference image whose alignment position has been corrected.

In accordance with another aspect of the present invention, a target workpiece inspection apparatus includes an optical image acquiring unit configured to acquire an optical image of a target workpiece to be inspected on which a pattern is formed, a reference image generating unit configured to generate a reference image to be compared with the optical image, a difference judging unit configured to judge whether an absolute value of difference between a pixel value of the optical image and a pixel value of the reference image in each pixel at a preliminary alignment position between the optical image and the reference image is smaller than a predetermined threshold value, a first SSD (Sum of Squared Difference) calculating unit configured to calculate a first displacement amount from the preliminary alignment position between the optical image and the reference image to a first position where an SSD between the pixel value of the optical image and the pixel value of the reference image is minimized, a least-squares method displacement calculating unit configured to calculate a second displacement amount displaced from the first position, by using a regular matrix for a least-squares method obtained from a result determined by the difference judging unit, a second SSD calculating unit configured to calculate an SSD between the pixel value of the optical image and the pixel value of the reference image at a second position displaced from the first position by the second displacement amount, an SSD judging unit configured to judge which of the SSD at the first position and the SSD at the second position is smaller, a position correcting unit configured to correct an alignment position between the optical image and the reference image to a position where a smaller SSD as a result determined by the SSD judging unit is obtained, and a comparing unit configured to compare the optical image and the reference image whose alignment position has been corrected.

In accordance with another aspect of the present invention, an image alignment method for aligning an optical image and a reference image for use in a comparing inspection of a target workpiece to be inspected on which a pattern is formed, includes judging whether an absolute value of difference between a pixel value of the optical image and a pixel value of the reference image in each pixel at a preliminary alignment position between the optical image and the reference image is smaller than a predetermined threshold value, calculating a first displacement amount from the preliminary alignment position between the optical image and the reference image to a first position where an SSD (Sum of Squared Difference) between the pixel value of the optical image and the pixel value of the reference image is minimized, calculating a second displacement amount displaced from the first position, by using a regular matrix for a least-squares method obtained from a result of the judging of difference, calculating an SSD between the pixel value of the optical image and the pixel value of the reference image at a second position displaced from the first position by the second displacement amount, judging which of the SSD at the first position and the SSD at the second position is smaller, and correcting an alignment position between the optical image and the reference image to a position where a smaller SSD as a result of the judging is obtained, to output a result of the correcting.

In accordance with another aspect of the present invention, a computer-readable recording medium with a program recorded thereon to be executed by a computer includes storing process for storing an optical image and a reference image for use in a comparing inspection of a target workpiece to be inspected on which a pattern is formed, in a storage device, difference judging process for judging whether an absolute value of difference between a pixel value of the optical image and a pixel value of the reference image in each pixel at a preliminary alignment position between the optical image and the reference image is smaller than a predetermined threshold value by reading the optical image and the reference image from the storage device, and least-squares method displacement calculating process for calculating a displacement amount based on a least-squares method by using a regular matrix for the least-squares method obtained from a result of the difference judging process, to output the displacement amount.

DETAILED DESCRIPTION OF THE INVENTION

Embodiment 1

Figure 1:
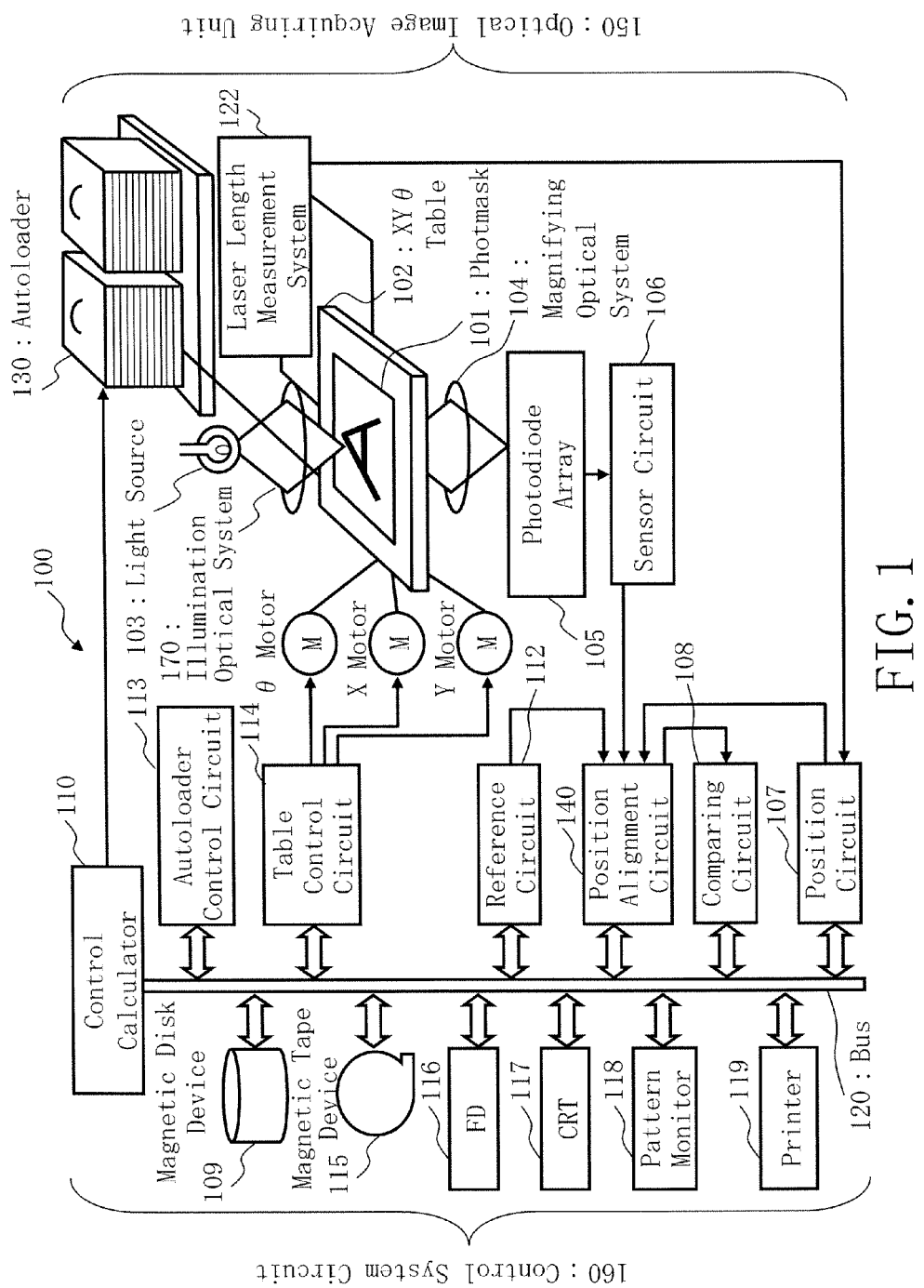
FIG. 1 is a schematic diagram showing the structure of a target workpiece inspection apparatus described in Embodiment 1.

FIG. 1 is a schematic diagram showing the configuration of a target workpiece inspection apparatus described in Embodiment 1. In the figure, a target workpiece inspection apparatus 100 that inspects a defect of a substrate, such as a mask or a wafer on which a pattern is formed, serving as a target workpiece includes an optical image acquiring unit 150 and a control system circuit 160. The optical image acquiring unit 150 includes an XYθ table 102, a light source 103, a magnifying optical system 104, a photodiode array 105, a sensor circuit 106, a laser length measurement system 122, an autoloader 130, and an illumination optical system 170. In the control system circuit 160, a control calculator 110 serving as a computer is connected, through a bus 120 serving as a data transmission path, to a position circuit 107, a comparing circuit 108, a reference circuit 112 being an example of a reference image generating unit, an alignment circuit 140, an autoloader control circuit 113, a table control circuit 114, a magnetic disk device 109, a magnetic tape device 115, a flexible disk device (FD) 116, a CRT 117, a pattern monitor 118, and a printer 119. The XYθ table 102 is driven by an X-axis motor, a Y-axis motor, and a θ-axis motor. In FIG. 1, only elements necessary for explaining Embodiment 1 are described, and others are not described. It should be understood that other constituent elements generally necessary for the target workpiece inspection apparatus 100 are included.

Figure 2:
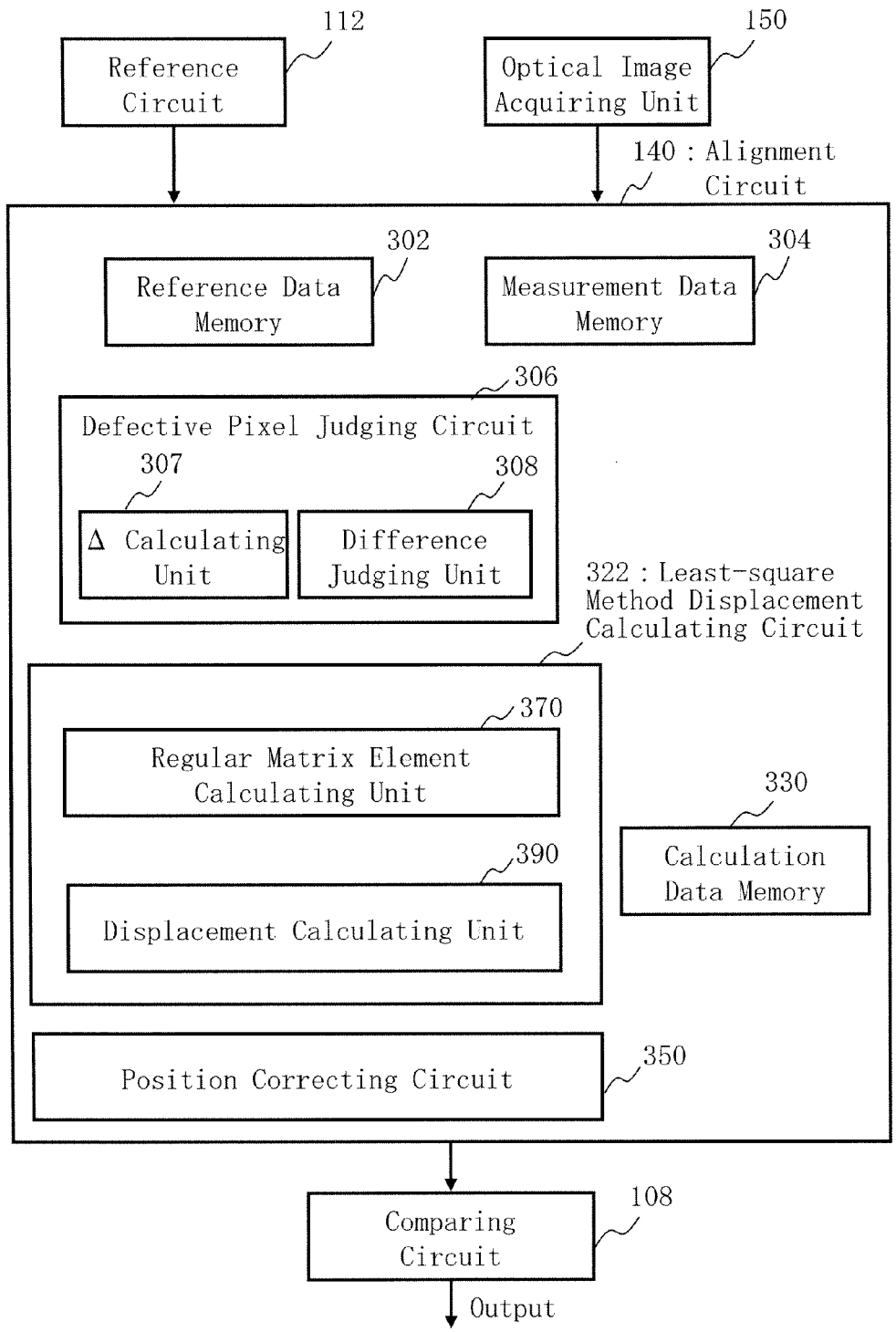
FIG. 2 is a block diagram showing the structure of an alignment circuit described in Embodiment 1.

FIG. 2 is a block diagram showing an example of the configuration of the alignment circuit in Embodiment 1. In the figure, the alignment circuit 140 includes a reference data memory 302, a measurement data memory 304, a defective pixel judging circuit 306, a least-squares method displacement calculating circuit 322, a calculation data memory 330, and a position correcting circuit 350. The defective pixel judging circuit 306 includes a Δ calculating unit 307 and a difference judging unit 308. The least-squares method displacement calculating circuit 322 includes a regular matrix, or "normal matrix" element calculating unit 370 and a displacement calculating unit 390. The alignment circuit 140 receives reference data from the reference circuit 112 and measurement data from the optical image acquiring unit 150, performs the alignment of these items of data, and outputs the reference data and the measurement data to the comparing circuit 108. The data etc. calculated in the alignment circuit 140 is stored in the calculation data memory 330 as needed.

Figure 3:
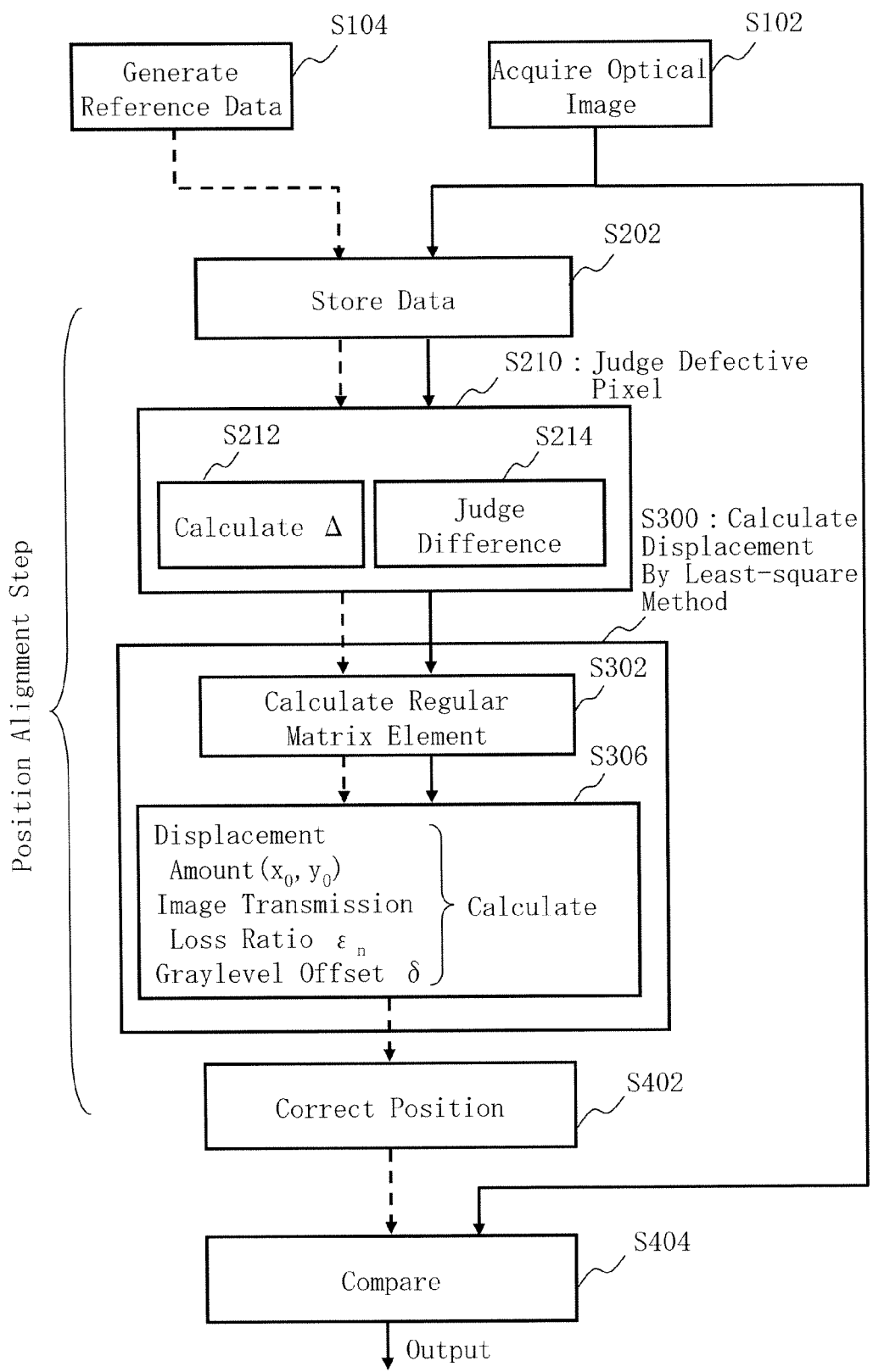
FIG. 3 is a flowchart showing main steps of a target workpiece inspection method described in Embodiment 1.

FIG. 3 is a flowchart showing main steps of a target workpiece inspection method described in Embodiment 1. In the figure, the target workpiece inspection method executes a series of steps including an optical image acquiring step (S102), a reference data generating step (S104), an alignment step, and a comparing step (S404). As the alignment step being one example of an image alignment method, a series of steps including a storing step (S202), a defective pixel judging step (S210), a least-squares method displacement calculating step (S300), and a position correcting step (S402) is executed. Furthermore, in the defective pixel judging step (S210), a series of steps including Δ calculating step (S212) and a difference judging step (S214) is executed. Moreover, in the least-squares method displacement calculating step (S300), a series of steps including a regular matrix element calculating step (S302), and a calculating step (S306) of a displacement amount, an image transmission loss ratio (or "image strength fluctuation rate"), and a graylevel offset is executed. In FIG. 3, a solid line shows a flow of measurement data (optical image), and a dotted line shows a flow of reference data.

In S (step) 102, as the optical image acquiring step, the optical image acquiring unit 150 acquires an optical image of a photomask 101 serving as a target workpiece on which a figure indicated by figure data included in design data is drawn based on the design data. More specifically, the optical image can be acquired as follows:

The photomask 101 serving as a target workpiece to be inspected is placed on the XYθ table 102 which is movable in a horizontal direction and a rotating direction by the X-, Y-, and θ-axis motors. The pattern written on the photomask 101 is irradiated with lights from the appropriate light source 103 arranged above the XYθ table 102. The photomask 101 serving as a target workpiece is irradiated with a flux of light from the light source 103, through the illumination optical system 170. Below the photomask 101, the magnifying optical system 104, the photodiode array 105, and the sensor circuit 106 are arranged. The light transmitted through the photomask 101 serving as a target workpiece such as an exposure mask is focused on the photodiode array 105 as an optical image, through the magnifying optical system 104 and enters the photodiode array 105.

Figure 4:
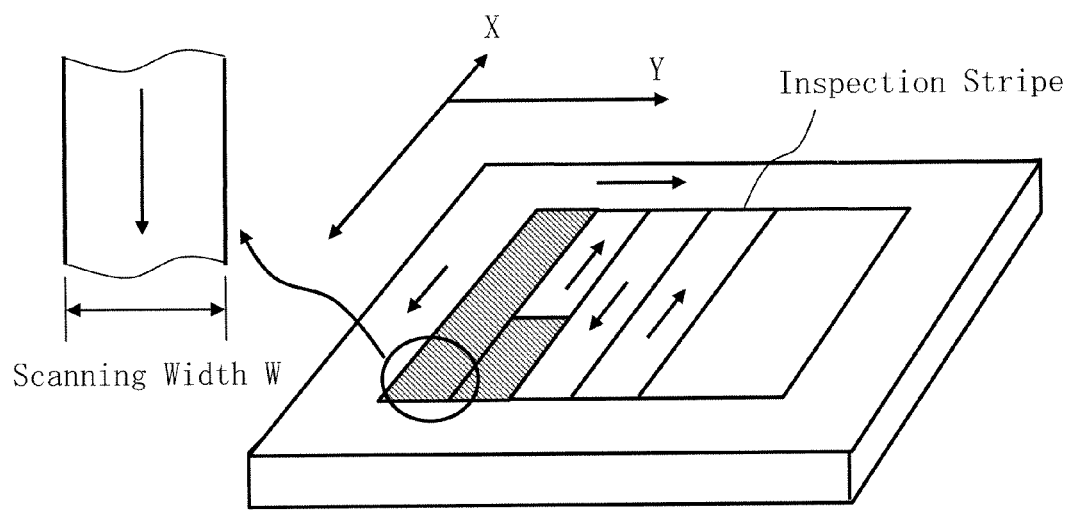
FIG. 4 shows a drawing for explaining procedures of acquiring an optical image described in Embodiment 1.

FIG. 4 shows a diagram for explaining a procedure for acquiring an optical image described in Embodiment 1. As shown in the figure, a region to be inspected is virtually divided into a plurality of strip-like inspection stripes, each of which has a scanning width W, in the Y direction. To acquire an optical image, the movement of the XYθ table 102 is controlled so that each of the divided inspection stripes can be continuously scanned, while moving in the X direction. In the photodiode array 105, images each having the scanning width W as shown in FIG. 4 are continuously input. After images on the first inspection stripe having been scanned, images each having the scanning width W are continuously input while an image on the second inspection stripe is moved in the reverse direction. When an image on the third inspection stripe is to be acquired, the image is scanned while the image is moved in the direction reverse to the direction for scanning the image on the second inspection stripe, i.e., the same direction for scanning the image on the first inspection stripe. Continuously acquiring images in this manner makes it possible to reduce wasteful processing time.

The image of the pattern focused on the photodiode array 105 is photoelectrically converted by the photodiode array 105. Furthermore, the electric image is A/D-converted (analog to digital converted) by the sensor circuit 106. In the photodiode array 105, a sensor such as a TDI (Time Delay Integration) sensor is arranged. The TDI sensor scans the image of the pattern of the photomask 101 serving as a target workpiece, by continuously moving the XYθ table 102 serving as a stage in the X-axis direction. The light source 103, the magnifying optical system 104, the photodiode array 105, and the sensor circuit 106 compose an inspection optical system having a large magnification.

The XYθ table 102 is driven by the table control circuit 114 under the control of the control calculator 110. The XYθ table 102 can be moved by a drive system such as a three-axis (X-Y-θ) motor which drives the XYθ table 102 in the X direction, the Y direction, and the θ direction.

Measurement data (optical image) output from the sensor circuit 106 is transmitted to the alignment circuit 140 together with data which is output from the position circuit 107 and indicates the position of the photomask 101 on the XYθ table 102. The measurement pattern data is, for example, 8-bit unsigned data, and indicates a graylevel of brightness of each pixel. The measurement data is compared with each image data of 512×512 pixels, for example.

Then, in step S104, as the reference data generating step, the reference circuit 112 generates reference data (reference image) for comparing with measurement data on the basis of design data of the photo mask 101 serving as a target workpiece to be inspected. The reference data to be compared is generated as image data of 512×512 pixels, for example, like the measurement data.

The reference data herein is generated based on the design data in order to execute a "die to database inspection", but it does not restricted to this. A "die to die inspection" can also be conducted, and in this case, reference data can be generated based on another measurement data (optical image) to be used for comparison.

Next, as the alignment step, aligning is performed for comparing the measurement data and the reference data.

In step S202, as the storing step, reference data, for each 512×512 pixels for example as stated above, is read using the control calculator 110 and stored in the reference data memory 302. In the same manner, measurement data, for each 512×512 pixels for example, is read and stored in the measurement data memory 304. Next, after judging a defective pixel, a least-squares method displacement calculation is performed. An amount of displacement needed for alignment is herein calculated using the least-squares method being a statistical method.

Supposing that a graylevel value of measurement data serving as an optical image (actual image) is S(x, y), a displacement amount in the directions of X and Y of the graylevel value (pixel value) S(x, y) of the measurement data is $(x_0, y_0)$, an image transmission loss ratio is $\epsilon^n$, a graylevel offset is δ, and a pixel number of each data is N+1, the equation (1) shown below can be obtained with respect to a graylevel value U(x, y) of reference data serving as a reference image.

$$S(x, y) = U(x - x_0, y - y_0) - \sum_{i=0}^{N} \epsilon_i U^{i+1}(x - x_0, y - y_0) - \delta \quad (1)$$

Moreover, by linearization on supposition that the fluctuation amount is small enough, the equation (2) shown below can be obtained.

$$U(x, y) - S(x, y) = x_0 \frac{\partial U}{\partial x} + y_0 \frac{\partial U}{\partial y} + \sum_{i=0}^{N} \epsilon_i U^{i+1} + \delta \quad (2)$$

wherein ∂U/∂x is a partial differential (space differentiation) of U by x, and ∂U/∂y is a partial differential (space differentiation) of U by y.

In the target workpiece inspection apparatus 100, the displacement amount $(x_0, y_0)$ in the directions X and Y, the image transmission loss ratio $\epsilon_n$, and the graylevel offset δ change depending upon apparatus features which are different from pattern defects.

Figure 5:
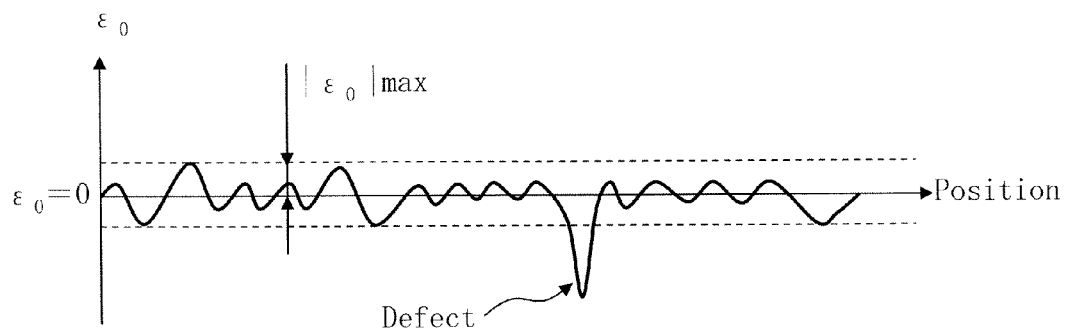
FIG. 5 shows an example of a change of an image transmission loss ratio described in Embodiment 1.

FIG. 5 shows an example of a change of the image transmission loss ratio described in Embodiment 1. When a change of the image transmission loss ratio of a test pattern is calculated beforehand by an experiment using the target workpiece inspection apparatus 100, the change such as the one shown in FIG. 5 occurs. If a pattern has a defect, especially a large defect compared with apparatus features, it changes largely as shown in FIG. 5.

Figure 6:
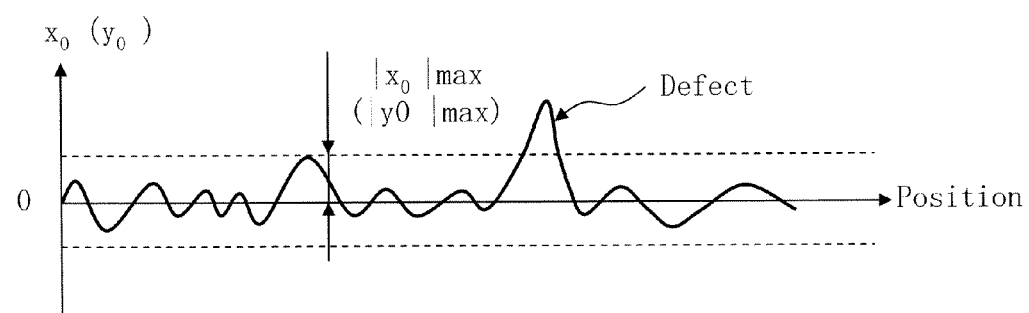
FIG. 6 shows an example of a displacement amount fluctuation described in Embodiment 1.

FIG. 6 shows an example of a displacement amount fluctuation described in Embodiment 1. When a change of the displacement amount ($x_0$ or $y_0$) in the X direction or Y direction of a test pattern is calculated beforehand by an experiment using the target workpiece inspection apparatus 100, the change such as the one shown in FIG. 6 occurs. If a pattern has a defect, especially a large defect compared with apparatus features, it changes largely as shown in FIG. 6 as well as the case of the image transmission loss ratio.

Figure 7:
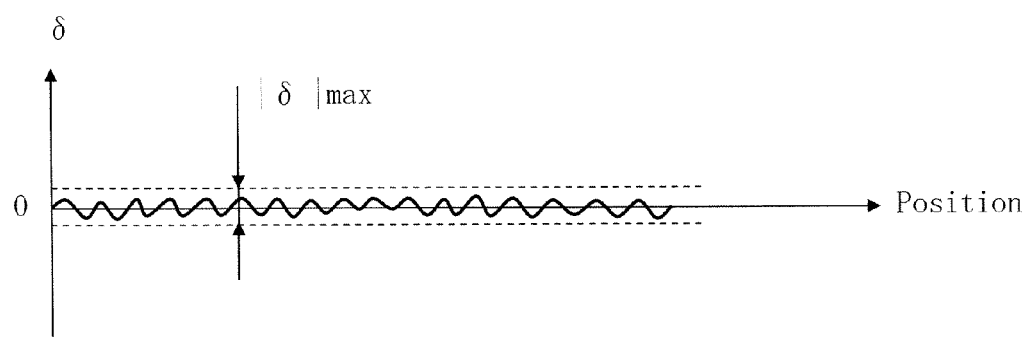
FIG. 7 shows an example of a graylevel offset fluctuation described in Embodiment 1.

FIG. 7 shows an example of a graylevel offset fluctuation described in Embodiment 1. When a change of the graylevel offset δ of a test pattern is calculated beforehand by an experiment using the target workpiece inspection apparatus 100, the change such as the one shown in FIG. 7 occurs.

As mentioned above, in the target workpiece inspection apparatus 100, the displacement amount $(x_0, y_0)$ in the directions X and Y, the image transmission loss ratio $\epsilon_n$, and the graylevel offset δ change for each pixel, depending upon apparatus features which are different from pattern defects. Then, when previously calculating the fluctuation generated depending upon apparatus features, with respect to a pixel of a predetermined number, by an experiment and calculating an absolute value of the maximum of the fluctuation range of each parameter, the equation (3) shown below can be obtained.

$$|U(x, y) - S(x, y)| < |x_0|_{max}\left|\frac{\partial U}{\partial x}\right| + |y_0|_{max}\left|\frac{\partial U}{\partial y}\right| + |\varepsilon_0|_{max}|U| + |\delta_{max}| \quad (3)$$

wherein the case of N=0 (0th order) is shown as an example, and the absolute value of the maximum of a fluctuation range of the displacement amount $x_0$ in the direction of X is $|x_0|_{max}$, the absolute value of the maximum of a fluctuation range of the displacement amount $y_0$ in the direction of Y is $|y_0|_{max}$, the absolute value of the maximum of a fluctuation range of the image transmission loss ratio $\varepsilon_0$ is $|\varepsilon_0|_{max}$, and the absolute value of the maximum of a fluctuation range of the graylevel offset $\delta$ is $|\delta|_{max}$.

In step S210, as the defective pixel judging step, the defective pixel judging circuit 306 judges a defective pixel using a predetermined threshold value, as shown below. Details of each step in the defective pixel judging are described below.

First, in step S212, as a threshold value $\Delta$ calculating step, the $\Delta$ calculating unit 307 calculates the threshold value $\Delta$ (an example of a predetermined threshold value) in the equation (4) shown below, with respect to each pixel at a preliminary alignment position between measurement data and reference data. A position tentatively in accordance in the data coordinate system can be used as the preliminary alignment position.

$$\Delta = |x_0|_{max}\left|\frac{\partial U}{\partial x}\right| + |y_0|_{max}\left|\frac{\partial U}{\partial y}\right| + |\varepsilon_0|_{max}|U| + |\delta|_{max} \quad (4)$$

The threshold value $\Delta$ includes the absolute value $|\varepsilon_0|_{max}$ of the maximum of the image transmission loss ratio which is generated from apparatus features, the absolute value $|x_0|_{max}$ of the maximum of the displacement amount in the direction of X which is generated from apparatus features, and the absolute value $|y_0|_{max}$ of the maximum of the displacement amount in the direction of Y which is generated from apparatus features, as parameters. Furthermore, the absolute value $|\delta|_{max}$ of the maximum of the fluctuation range of the graylevel offset $\delta$ is also included. As shown in the equation (4), the threshold value $\Delta$ can be obtained by adding the following (a) to (d):

(a) a value obtained by multiplying $|\varepsilon_0|_{max}$ by an absolute value $|U|$ of the graylevel of reference data, (b) a value obtained by multiplying $|x_0|_{max}$ by the absolute value $|\partial U/\partial x|$ of the first differential value ($\partial U/\partial x$) which is calculated by space differentiating reference data in the direction of X, (c) a value obtained by multiplying $|y_0|_{max}$ by the absolute value $\partial \partial U/\partial y|$ of the second differential value ($\partial U/\partial y$) which is calculated by space differentiating reference data in the direction of Y, and (d) $|\delta|_{max}$.

By calculating the threshold value $\Delta$ as mentioned above, it is possible to perform judgment as follows. In step S214, as the difference judging step, the difference judging unit 308 judges whether an absolute value of difference between the graylevel of measurement data and the graylevel of reference data in each pixel at a preliminary alignment position between the measurement data and the reference data is smaller than the threshold value $\Delta$ or not as shown in the equation (5).

$$|U(x,y)-S(x,y)|<\Delta \quad (5)$$

As mentioned above, when $|\varepsilon_0|_{max}$, $|x_0|_{max}$, $|y_0|_{max}$, and $|\delta|_{max}$ are calculated as parameters beforehand by an experiment, it is possible to judge with respect to each pixel whether an absolute value of difference between the graylevel of measurement data and the graylevel of reference data is smaller than the threshold value $\Delta$ or not. Thereby, when the absolute value of difference is smaller than the threshold value $\Delta$, it turns out that a large defect exceeding the fluctuation range of at least one of the parameters does not exist in the pixel. On the other hand, if the absolute value of difference in not smaller than the threshold value $\Delta$, it turns out that a large defect is included in the pixel.

Although $|\delta|_{max}$ is included in the threshold value $\Delta$ in the equation (4), the threshold value $\Delta$ not including $|\delta|_{max}$ as shown in (6) is also acceptable.

$$\Delta = |x_0|_{max}\left|\frac{\partial U}{\partial x}\right| + |y_0|_{max}\left|\frac{\partial U}{\partial y}\right| + |\varepsilon_0|_{max}|U| \quad (6)$$

Since $|\delta|_{max}$ is a small value compared with other values, it is both acceptable to include it or not to include it. On the contrary, though only the 0th order term is taken into account in the equation (4), high order terms $|\varepsilon_1|_{max}$ to $|\varepsilon_N|_{max}$ can also be included. Since the threshold value $\Delta$ becomes large by including a high order term, the inspection accuracy can be lowered.

In step S300, as the least-squares method displacement calculating step, the least-squares method displacement calculating circuit 322 calculates a displacement amount $(x_0, y_0)$ displaced from the preliminary alignment position by using the regular matrix for the least-squares method which is obtained from the result of the difference judging. Moreover, in the least-squares method displacement calculating step, an element the regular matrix is calculated.

In step S302, as the regular matrix element calculating step, the regular matrix element calculating unit 370 calculates a plurality of elements of the regular matrix for the least-squares method, for calculating a displacement amount $(x_0, y_0)$ displaced from the preliminary alignment position between the measurement data and the reference data. Specifically, with respect to each pixel of a two-dimensional image, a graylevel value $U(x, y)$ of reference data, a value $(U-S)$ obtained by subtracting a graylevel of the measurement data serving as an actual image from a graylevel of the reference data, a value $(\partial U/\partial x)$ obtained by space differentiating the graylevel of the reference data in the X direction, and a value $(\partial U/\partial y)$ obtained by space differentiating the graylevel of the reference data in the Y direction are calculated to obtain each element of the equation (7) of the correlation matrix shown below. Moreover, as the preliminary alignment position, a position tentatively in accordance in the data coordinate system can be used.

$$\begin{pmatrix} \sum \left(\frac{\partial U}{\partial x}\right)^2 & \sum \frac{\partial U}{\partial x} \cdot \frac{\partial U}{\partial y} & \sum \frac{\partial U}{\partial x} \cdot U & \cdots & \sum \frac{\partial U}{\partial x} \cdot U^N & \sum \frac{\partial U}{\partial x} \\ \sum \frac{\partial U}{\partial y} \cdot \frac{\partial U}{\partial x} & \sum \left(\frac{\partial U}{\partial y}\right)^2 & \sum \frac{\partial U}{\partial y} \cdot U & \cdots & \sum \frac{\partial U}{\partial y} \cdot U^N & \sum \frac{\partial U}{\partial y} \\ \sum U \cdot \frac{\partial U}{\partial x} & \sum U \cdot \frac{\partial U}{\partial y} & \sum U^2 & \cdots & \sum U^{N+1} & \sum U \\ \vdots & \vdots & \vdots & & \vdots & \vdots \\ \sum U^N \cdot \frac{\partial U}{\partial x} & \sum U^N \cdot \frac{\partial U}{\partial y} & \sum U^{N+1} & \cdots & \sum U^{2N} & \sum U^N \\ \sum \frac{\partial U}{\partial x} & \sum \frac{\partial U}{\partial y} & \sum U & \cdots & \sum U^N & 1 \end{pmatrix} \begin{pmatrix} x_0 \\ y_0 \\ \varepsilon_0 \\ \vdots \\ \varepsilon_N \\ \delta \end{pmatrix} = \begin{pmatrix} \frac{\partial U}{\partial x}(U-S) \\ \frac{\partial U}{\partial y}(U-S) \\ \sum U(U-S) \\ \vdots \\ \sum U^N(U-S) \\ \sum (U-S) \end{pmatrix} \quad (7)$$

In Embodiment 1, when calculating each element, a pixel whose absolute value |U−S| of difference is not smaller than the threshold value Δ is deleted from the element calculation of a regular matrix. Thus, by excluding the pixel corresponding to a large defect from the element calculation, it becomes possible to avoid excessively correcting a value of each element because of being affected by the pixel corresponding to a large defect. In other words, in the regular matrix in Embodiment 1, a product-sum term corresponding to a pixel whose absolute value of difference is equal to or larger than a predetermined threshold value is deleted from the product-sum calculation for acquiring all the elements of the regular matrix.

In step S306, as the calculating step of a displacement amount, an image transmission loss ratio, and a graylevel offset, which is an example of a displacement amount calculating step, the displacement calculating unit 390 solves simultaneous equations using a regular matrix for the least-squares method obtained from a result of the difference judging. By performing such a simultaneous equation solution step, a displacement amount ($x_0$, $y_0$) displaced from a preliminary alignment position obtained by the least-squares method, an image transmission loss ratio $\epsilon_0$ to $\epsilon_N$ and a graylevel offset δ can be calculated. In the above explanation, description relating to each value of the matrix is partially omitted in the equation (7).

As mentioned above, by solving the simultaneous equations (7) taking account of a pixel whose value is not smaller than the threshold value Δ, it is possible to obtain a displacement amount ($x_0$, $y_0$) in the directions of X and Y, an image transmission loss ratio $\epsilon_0$ to $\epsilon_N$ and a graylevel offset δ from which the influence of a large defect pixel is removed.

In the pattern whose whole imaging range serves as a pattern (zero dimensional pattern) such as a so-called overall pattern, the displacement amount ($x_0$, $y_0$) in the directions X and Y should intrinsically become indeterminate. Actually, however, there is a case that a wrong value has been calculated as a solution, by an influence of a noise etc. Moreover, for example, in the pattern which spreads in one direction (one-dimensional pattern), such as a so-called line and space pattern (line & space pattern), the displacement amount ($x_0$ or $y_0$) in the direction X or Y should intrinsically become indeterminate. Actually, however, there is a case that an unstable value is figured out as a clear solution. Thus, in the case of these patterns, what is necessary is just to delete, according to need, an element of the regular matrix which includes a differentiation value (∂U/∂x) and a differentiation value (∂U/∂y). Thereby, a solution which should intrinsically be indeterminate can be eliminated.

In step S402, as the position correcting step, the position correcting circuit 350 (an example of a position correcting unit) corrects an alignment position between measurement data and reference data from the preliminary alignment position to the position obtained by performing displacing by the displacement amount from the preliminary alignment position. In the case $x_0$ or $y_0$ being an indeterminate solution, the preliminary alignment position can be used without changing, with respect to the indeterminate solution. It is also preferable for the position correcting circuit 350 to correct the image strength of each pixel of reference data using the image transmission loss ratio $\epsilon_0$ to $\epsilon_N$ calculated by the least-squares method displacement calculating circuit 322.

Figure 8A:
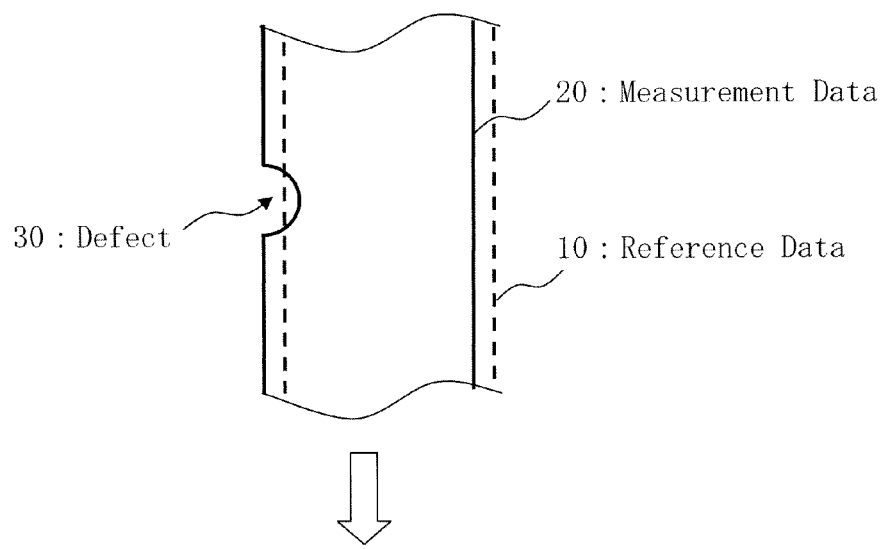
FIGS. 8A and 8B show a drawing for explaining a manner of positional alignment described in Embodiment 1.
Figure 8B:
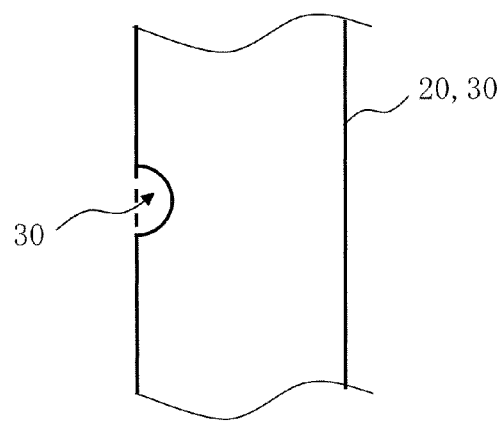

FIG. 8A and FIG. 8B show drawings for explaining a manner of the position alignment described in Embodiment 1. The figures show the case where a large defect 30 exists in a measurement data 20. In this case, if a value of the pixel of the large defect 30 is not taken into account, a reference data 10 will be excessively aligned because of being affected by the large defect 30. As a result, as shown in FIG. 8A, the positions of the measurement data 20 and the reference data 10 are out of alignment with each other. On the other hand, when calculating elements of a regular matrix while excluding the pixel of the large defect 30, alignment of the measurement data 20 and the reference data 10 can be highly accurately executed as shown in FIG. 8B since it is possible to perform the position alignment while disregarding the pixel of the large defect 30. Then, the result of the correcting is output to the comparing circuit 108.

In step S404, as the comparing step, the comparing circuit 108 aligns, by means of the position alignment circuit 140, the measurement data serving as a pattern image to be inspected generated by the sensor circuit 106 on the basis of the transfer image obtained from the photo mask 101, and the reference data serving as an inspection standard pattern image generated by the reference circuit 112, and takes in both the data. Then, the comparing circuit 108 compares them, namely the taken measurement data and reference data, with each other according to a predetermined algorithm, and judges whether there is a defect or not. The comparing circuit 108 outputs the result of the comparing. Thus, by performing a data comparison through such a highly precise alignment, it is possible to prevent a false detection of a defect and to decrease pseudo defects, thereby performing a highly precise inspection.

Embodiment 2

A method of correcting a local displacement in a frame will be explained in Embodiment 2.

Figure 9:
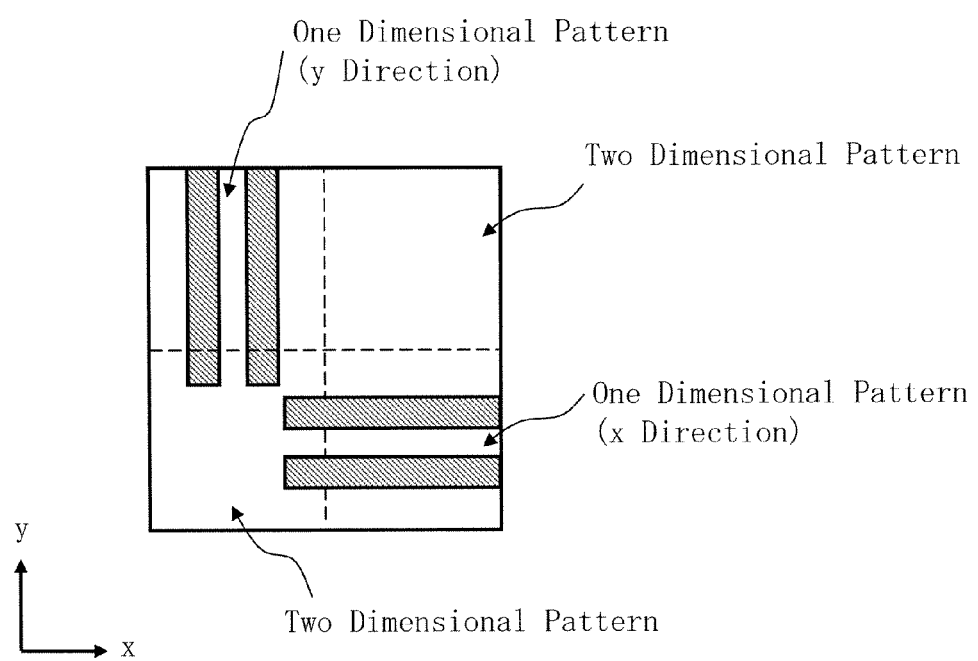
FIG. 9 shows an example of a two-dimensional pattern described in Embodiment 2.

FIG. 9 shows an example of a two-dimensional pattern described in Embodiment 2. For example, the case where a local displacement occurs in a part of the two-dimensional pattern shown in FIG. 9 will be explained. In the least-squares method, it is preferable to divide such a frame by dot lines as shown in FIG. 9 for example, to calculate a displacement amount and an image transmission loss ratio for each of the divided areas, and to estimate the displacement amount and the image transmission loss ratio, respectively. In such a case, when the divided areas are configured by a zero dimensional pattern, regular matrices can be degenerated to make $x_0$ and $y_0$ become indeterminate, as stated above. Similarly, when the divided areas are configured by a one-dimensional pattern, regular matrices can be degenerated respectively to make either $x_0$ or $y_0$ become indeterminate. Consequently, it is possible to perform a highly precise displacement correction by composing the respective divided areas.

Further, in the least-squares method, when dividing the above-mentioned frame by dot lines as shown in FIG. 8, it is also preferable to divide the frame by weighting, to calculate a displacement amount for each of the divided areas, and to estimate the displacement amount and the image transmission loss ratio, respectively.

Figure 10:
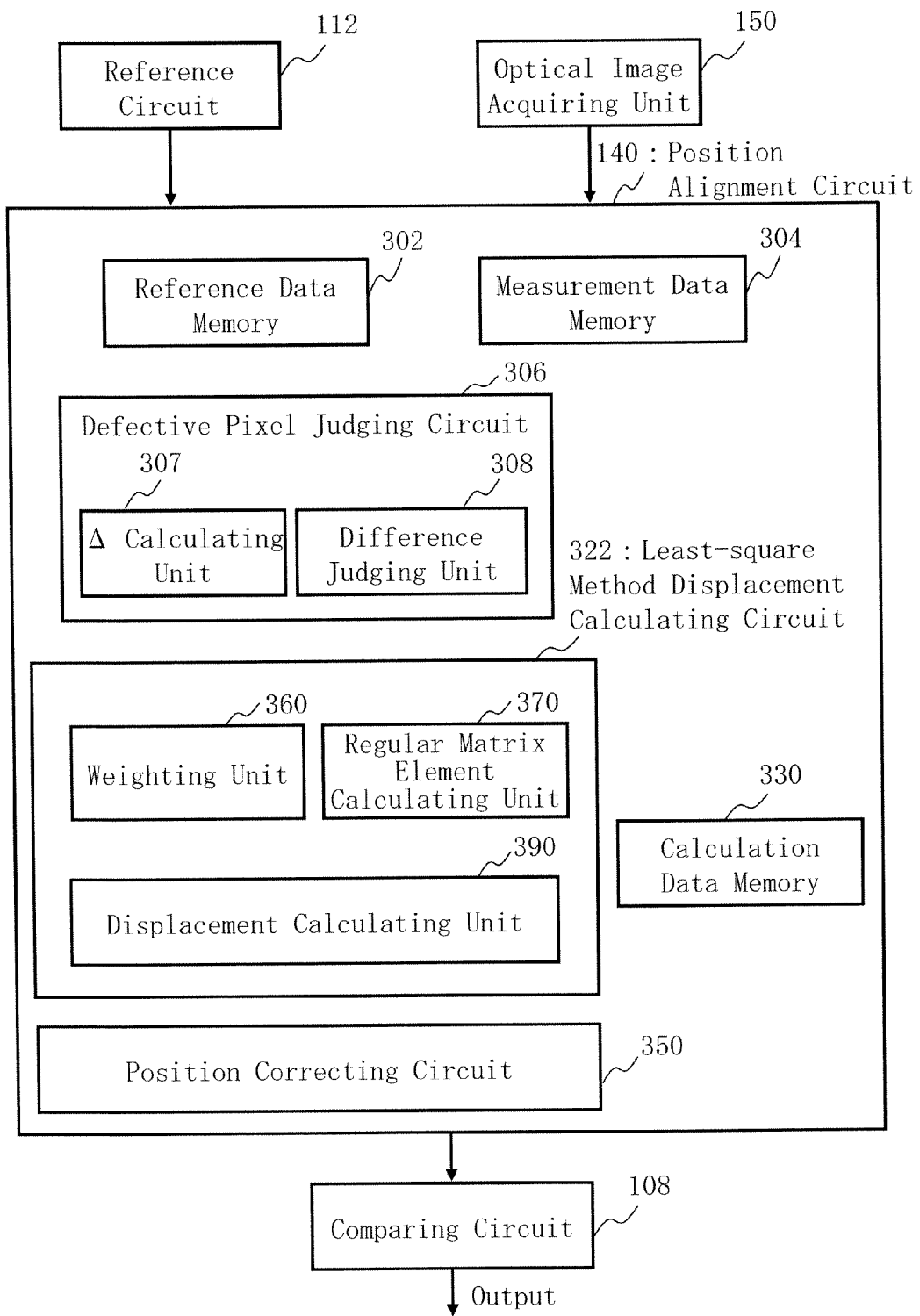
FIG. 10 is a block diagram showing the structure of an alignment circuit described in Embodiment 2.

FIG. 10 is a block diagram showing the structure of the alignment circuit in Embodiment 2. In the figure, the alignment circuit 140 further includes a weighting unit 360 in the least-squares method displacement calculating circuit 322 in addition to the structure shown in FIG. 2. Namely, FIG. 10 is the same as FIG. 2 except for the weighting unit 360 added.

Figure 11:
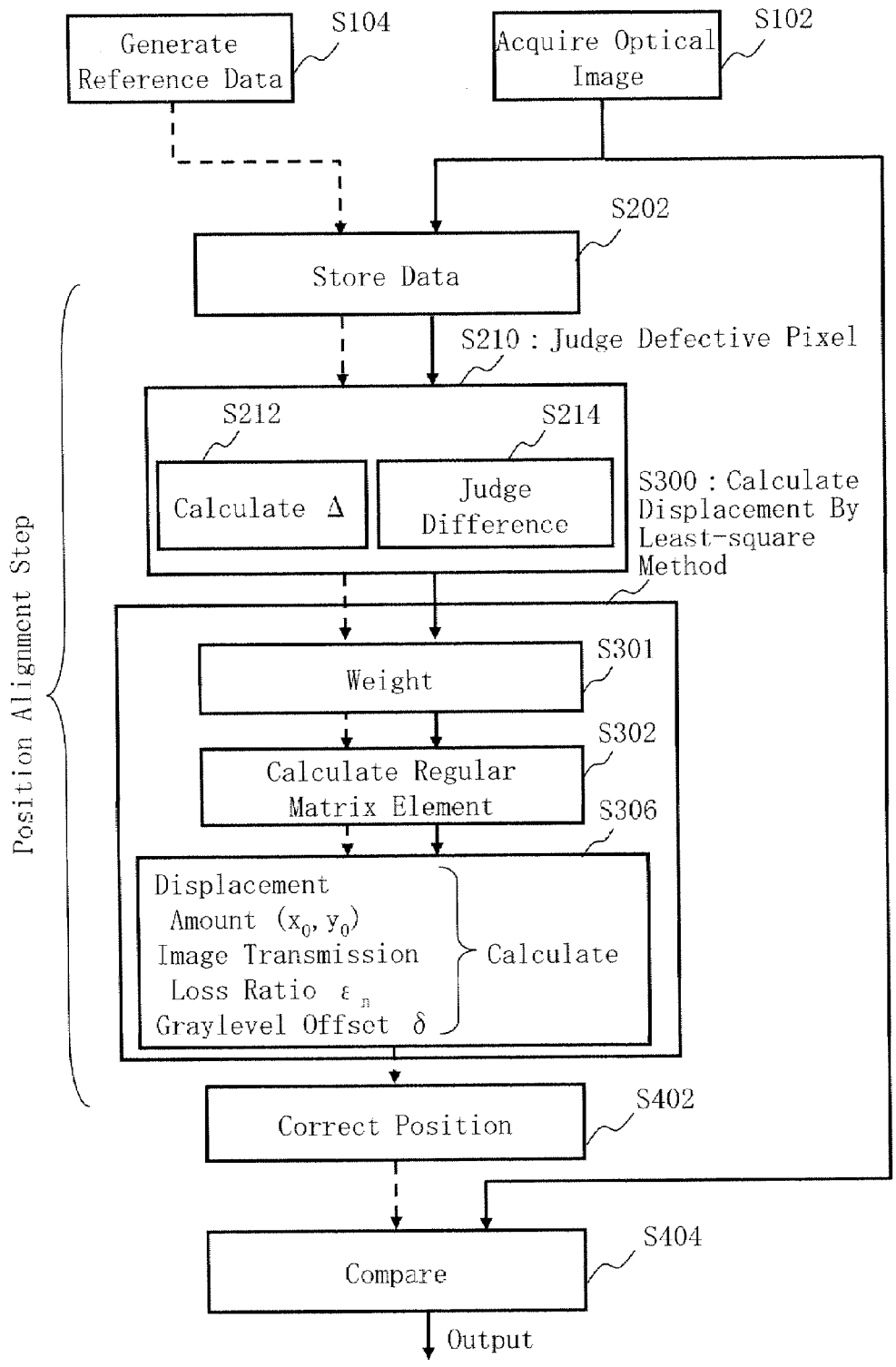
FIG. 11 is a flowchart showing main steps of a target workpiece inspection method described in Embodiment 2.

FIG. 11 is a flowchart showing main steps of a target workpiece inspection method described in Embodiment 2. In the figure, a weighting step (S301) is added before the regular matrix element calculating step (S302) in the least-squares method displacement calculating step (S300) in addition to the steps shown in FIG. 3. Namely, FIG. 11 is the same as FIG. 3 except for the weighting step S301 added. Furthermore, each step of the apparatus structure and the target workpiece inspection method or the image alignment method in Embodiment 2 is the same as that of Embodiment 1.

In step S301, as the weighting step, the weighting unit 360 calculates a weighting factor for performing weighting by one-dimensional linear interpolation. The weighting unit 360 calculates a value multiplied by the weighting factor with respect to each graylevel value of reference data.

Figure 12:
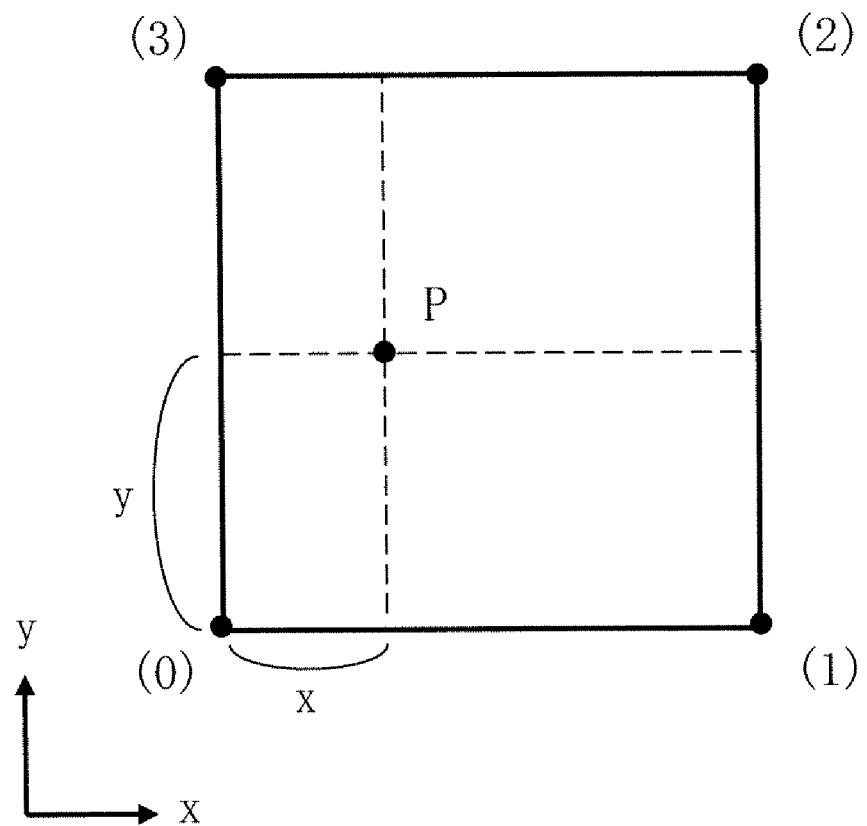
FIG. 12 shows a drawing for explaining weighting with two-dimensional linear interpolation described in Embodiment 2.

FIG. 12 is a drawing for explaining weighting by one-dimensional linear interpolation in Embodiment 2. The case where weighting is performed at neighboring four points will now be explained. For example, with regard to certain image data P, when a pixel P is interpolated by use of image data of four points (0, 1, 2, 3) therearound, the following equation (8) can be defined.

$$\begin{cases} U_{(0)} = (1-x)(1-y)U = W_{(0)}U \\ U_{(1)} = x(1-y)U = W_{(1)}U \\ U_{(2)} = xyU = W_{(2)}U \\ U_{(3)} = (1-x)yU = W_{(3)}U \end{cases} \quad (8)$$

That is, as shown in a method (8), a graylevel value $U_{(0)}$ of reference data can be expressed by $U_{(0)}=(1-x)(1-y)U$. When $(1-x)(1-y)$ expresses a weighting factor $W_{(0)}$, the graylevel value can be expressed as $U_{(0)}=W_{(0)}U$. Moreover, reference data $U_{(1)}$ can be expressed by $U_{(1)}=x(1-y)U$. When $x(1-y)$ expresses a weighting factor $W_{(1)}$, the reference data can be expressed as $U_{(1)}=W_{(1)}U$. Moreover, reference data $U_{(2)}$ can be expressed by $U_{(2)}=xyU$. When $xy$ expresses a weighting factor $W_{(2)}$, the reference data can be expressed as $U_{(2)}=W_{(2)}U$. Moreover, reference data $U_{(3)}$ can be expressed by $U_{(3)}=(1-x)yU$. When $(1-x)y$ expresses a weighting factor $W_{(3)}$, the reference data can be expressed as $U_{(3)}=W_{(3)}U$. Thus, if a correlation matrix is calculated by use of the weighted reference data $U_{(0)}$, reference data $U_{(1)}$, reference data $U_{(2)}$, and reference data $U_{(3)}$, the correlation matrix can be shown as the equation (9).

$$\begin{pmatrix} a & b & c & d \\ e & f & g & h \\ i & j & k & l \\ m & n & p & q \end{pmatrix} \begin{pmatrix} A \\ B \\ C \\ D \end{pmatrix} = \begin{pmatrix} A' \\ B' \\ C' \\ D' \end{pmatrix} \quad (9)$$

where each element a to d in the equation (9) can be expressed as the following equation (10).

$$\begin{cases} a = \begin{pmatrix} \sum \left(\frac{\partial U_{(0)}}{\partial x}\right)^2 & \cdots & \sum \frac{\partial U_{(0)}}{\partial x}\frac{\partial U_{(3)}}{\partial x} \\ \vdots & \ddots & \vdots \\ \sum \frac{\partial U_{(3)}}{\partial x}\frac{\partial U_{(0)}}{\partial x} & \cdots & \sum \left(\frac{\partial U_{(3)}}{\partial x}\right)^2 \end{pmatrix}, & c = \begin{pmatrix} \sum \frac{\partial U_{(0)}}{\partial x}U_{(0)} & \cdots & \sum \frac{\partial U_{(0)}}{\partial x}U_{(3)}^N \\ \vdots & \ddots & \vdots \\ \sum \frac{\partial U_{(3)}}{\partial x}U_{(0)} & \cdots & \sum \frac{\partial U_{(3)}}{\partial x}U_{(3)}^N \end{pmatrix} \\ b = \begin{pmatrix} \sum \frac{\partial U_{(0)}}{\partial x}\frac{\partial U_{(0)}}{\partial y} & \cdots & \sum \frac{\partial U_{(0)}}{\partial x}\frac{\partial U_{(3)}}{\partial y} \\ \vdots & \ddots & \vdots \\ \sum \frac{\partial U_{(3)}}{\partial x}\frac{\partial U_{(0)}}{\partial y} & \cdots & \sum \frac{\partial U_{(3)}}{\partial x}\frac{\partial U_{(3)}}{\partial y} \end{pmatrix}, & d = \begin{pmatrix} \sum \frac{\partial U_{(0)}}{\partial x}W_{(0)} & \cdots & \sum \frac{\partial U_{(0)}}{\partial x}W_{(3)} \\ \vdots & \ddots & \vdots \\ \sum \frac{\partial U_{(3)}}{\partial x}W_{(0)} & \cdots & \sum \frac{\partial U_{(3)}}{\partial x}W_{(3)} \end{pmatrix} \end{cases} \quad (10)$$

Moreover, each element e to h in the equation (9) can be expressed as the following equation (11).

$$\begin{cases} e = \begin{pmatrix} \sum \frac{\partial U_{(0)}}{\partial y}\frac{\partial U_{(0)}}{\partial x} & \cdots & \sum \frac{\partial U_{(0)}}{\partial y}\frac{\partial U_{(3)}}{\partial x} \\ \vdots & \ddots & \vdots \\ \sum \frac{\partial U_{(3)}}{\partial y}\frac{\partial U_{(0)}}{\partial x} & \cdots & \sum \frac{\partial U_{(3)}}{\partial y}\frac{\partial U_{(3)}}{\partial x} \end{pmatrix}, & g = \begin{pmatrix} \sum \frac{\partial U_{(0)}}{\partial y}U_{(0)} & \cdots & \sum \frac{\partial U_{(0)}}{\partial y}U_{(3)}^N \\ \vdots & \ddots & \vdots \\ \sum \frac{\partial U_{(3)}}{\partial y}U_{(0)} & \cdots & \sum \frac{\partial U_{(3)}}{\partial y}U_{(3)}^N \end{pmatrix} \\ f = \begin{pmatrix} \sum \left(\frac{\partial U_{(0)}}{\partial y}\right)^2 & \cdots & \sum \frac{\partial U_{(0)}}{\partial y}\frac{\partial U_{(3)}}{\partial y} \\ \vdots & \ddots & \vdots \\ \sum \frac{\partial U_{(3)}}{\partial y}\frac{\partial U_{(0)}}{\partial y} & \cdots & \sum \left(\frac{\partial U_{(3)}}{\partial y}\right)^2 \end{pmatrix}, & h = \begin{pmatrix} \sum \frac{\partial U_{(0)}}{\partial y}W_{(0)} & \cdots & \sum \frac{\partial U_{(0)}}{\partial y}W_{(3)} \\ \vdots & \ddots & \vdots \\ \sum \frac{\partial U_{(3)}}{\partial y}W_{(0)} & \cdots & \sum \frac{\partial U_{(3)}}{\partial y}W_{(3)} \end{pmatrix} \end{cases} \quad (11)$$

Moreover, each element i to l in the equation (9) can be expressed as the following equation (12).

$$\begin{cases} i = \begin{pmatrix} \sum U_{(0)}\frac{\partial U_{(0)}}{\partial x} & \cdots & \sum U_{(0)}\frac{\partial U_{(3)}}{\partial x} \\ \vdots & \ddots & \vdots \\ \sum U_{(3)}^N\frac{\partial U_{(0)}}{\partial x} & \cdots & \sum U_{(3)}^N\frac{\partial U_{(3)}}{\partial x} \end{pmatrix}, & k = \begin{pmatrix} \sum U_{(0)}^2 & \cdots & \sum U_{(0)}U_{(3)}^N \\ \vdots & \ddots & \vdots \\ \sum U_{(3)}^N U_{(0)} & \cdots & \sum U_{(3)}^{2N} \end{pmatrix} \\ j = \begin{pmatrix} \sum U_{(0)}\frac{\partial U_{(0)}}{\partial y} & \cdots & \sum U_{(0)}\frac{\partial U_{(3)}}{\partial y} \\ \vdots & \ddots & \vdots \\ \sum U_{(3)}^N\frac{\partial U_{(0)}}{\partial y} & \cdots & \sum U_{(3)}^N\frac{\partial U_{(3)}}{\partial y} \end{pmatrix}, & l = \begin{pmatrix} \sum U_{(0)}W_{(0)} & \cdots & \sum U_{(0)}W_{(3)} \\ \vdots & \ddots & \vdots \\ \sum U_{(3)}W_{(0)} & \cdots & \sum U_{(3)}W_{(3)} \end{pmatrix} \end{cases} \quad (12)$$

Moreover, each element m to q in the equation (9) can be expressed as the following equation (13).

$$\begin{cases} m = \begin{pmatrix} \sum W_{(0)}\frac{\partial U_{(0)}}{\partial x} & \cdots & \sum W_{(0)}\frac{\partial U_{(3)}}{\partial x} \\ \vdots & \ddots & \vdots \\ \sum W_{(3)}^N\frac{\partial U_{(0)}}{\partial x} & \cdots & \sum W_{(3)}^N\frac{\partial U_{(3)}}{\partial x} \end{pmatrix}, & p = \begin{pmatrix} \sum W_{(0)}U_{(0)} & \cdots & \sum W_{(0)}U_{(3)}^N \\ \vdots & \ddots & \vdots \\ \sum W_{(3)}^N U_{(0)} & \cdots & \sum W_{(3)}U_{(3)} \end{pmatrix} \\ n = \begin{pmatrix} \sum W_{(0)}\frac{\partial U_{(0)}}{\partial y} & \cdots & \sum W_{(0)}\frac{\partial U_{(3)}}{\partial y} \\ \vdots & \ddots & \vdots \\ \sum W_{(3)}\frac{\partial U_{(0)}}{\partial y} & \cdots & \sum W_{(3)}\frac{\partial U_{(3)}}{\partial y} \end{pmatrix}, & q = \begin{pmatrix} \sum W_{(0)}^2 & \cdots & \sum W_{(0)}W_{(3)} \\ \vdots & \ddots & \vdots \\ \sum W_{(3)}W_{(0)} & \cdots & \sum W_{(3)}^2 \end{pmatrix} \end{cases} \quad (13)$$

Moreover, each element A to D in the equation (9) can be expressed as the following equation (14).

$$\begin{cases} A = \begin{pmatrix} x_{0(0)} \\ \vdots \\ x_{0(3)} \end{pmatrix}, & C = \begin{pmatrix} \varepsilon_{0(0)} \\ \vdots \\ \varepsilon_{N(3)} \end{pmatrix} \\ B = \begin{pmatrix} y_{0(0)} \\ \vdots \\ y_{0(3)} \end{pmatrix}, & D = \begin{pmatrix} \delta_{(0)} \\ \vdots \\ \delta_{(3)} \end{pmatrix} \end{cases} \quad (14)$$

Moreover, each element A' to D' in the equation (9) can be expressed as the following equation (15).

$$\begin{cases} A' = \begin{pmatrix} \sum \frac{\partial U_{(0)}}{\partial x}(U_{(0)} - S_{(0)}) \\ \vdots \\ \sum \frac{\partial U_{(3)}}{\partial x}(U_{(3)} - S_{(3)}) \end{pmatrix}, & C' = \begin{pmatrix} \sum U_{(0)}(U_{(0)} - S_{(0)}) \\ \vdots \\ \sum U_{(3)}^N(U_{(3)} - S_{(3)}) \end{pmatrix} \\ B' = \begin{pmatrix} \sum \frac{\partial U_{(0)}}{\partial y}(U_{(0)} - S_{(0)}) \\ \vdots \\ \sum \frac{\partial U_{(3)}}{\partial y}(U_{(3)} - S_{(3)}) \end{pmatrix}, & D' = \begin{pmatrix} \sum W_{(0)}(U_{(0)} - S_{(0)}) \\ \vdots \\ \sum W_{(3)}(U_{(3)} - S_{(3)}) \end{pmatrix} \end{cases} \quad (15)$$

As mentioned above, when weighting is performed at neighboring four points, the correlation matrix equations shown in equations (9) to (15) are solved to obtain 4(N+4) variables, such as image transmission loss ratios $\varepsilon_{(0)}$ to $\varepsilon_{N(3)}$, displacement amounts $x_{0(0)}$, $x_{0(1)}$, $x_{0(2)}$, $x_{0(3)}$, $y_{0(0)}$, $y_{0(1)}$, $y_{0(2)}$, and $y_{0(3)}$, and graylevel offsets $\delta_{(0)}$ to $\delta_{(3)}$. When indeterminate solutions exist, it should be understood that the number of the indeterminate solutions are to be excluded. Position correction can be performed by use of such values to correct a local displacement and the like in the frame. Causes of the local displacement may include (1) meandering of the XY stage, (2) a pixel size difference between an actual image and a reference image, and (3) a pixel size difference between image scanning elements. The weighting method is not limited to the one using neighboring 4 points. It is also preferable to adopt bicubic interpolation using 16 points or the like. In the equations (1) to (15), description of values of the matrix is partly omitted.

Embodiment 3

In Embodiments 1 and 2 mentioned above, as the alignment method, a displacement amount calculated by the least-squares method displacement calculation in which dimension is judged and a correlation matrix is made to be rank deficient according to a pattern type is used. In Embodiment 3, in addition to the least-squares method mentioned above, an alignment method where a SSD (Sum of the Squared Difference) method is combined with the least-squares method will be explained. Specifically, the case where a sub-pixel unit SSD calculation and the least-squares method displacement calculation are performed in parallel will be described in Embodiment 3.

Figure 13:
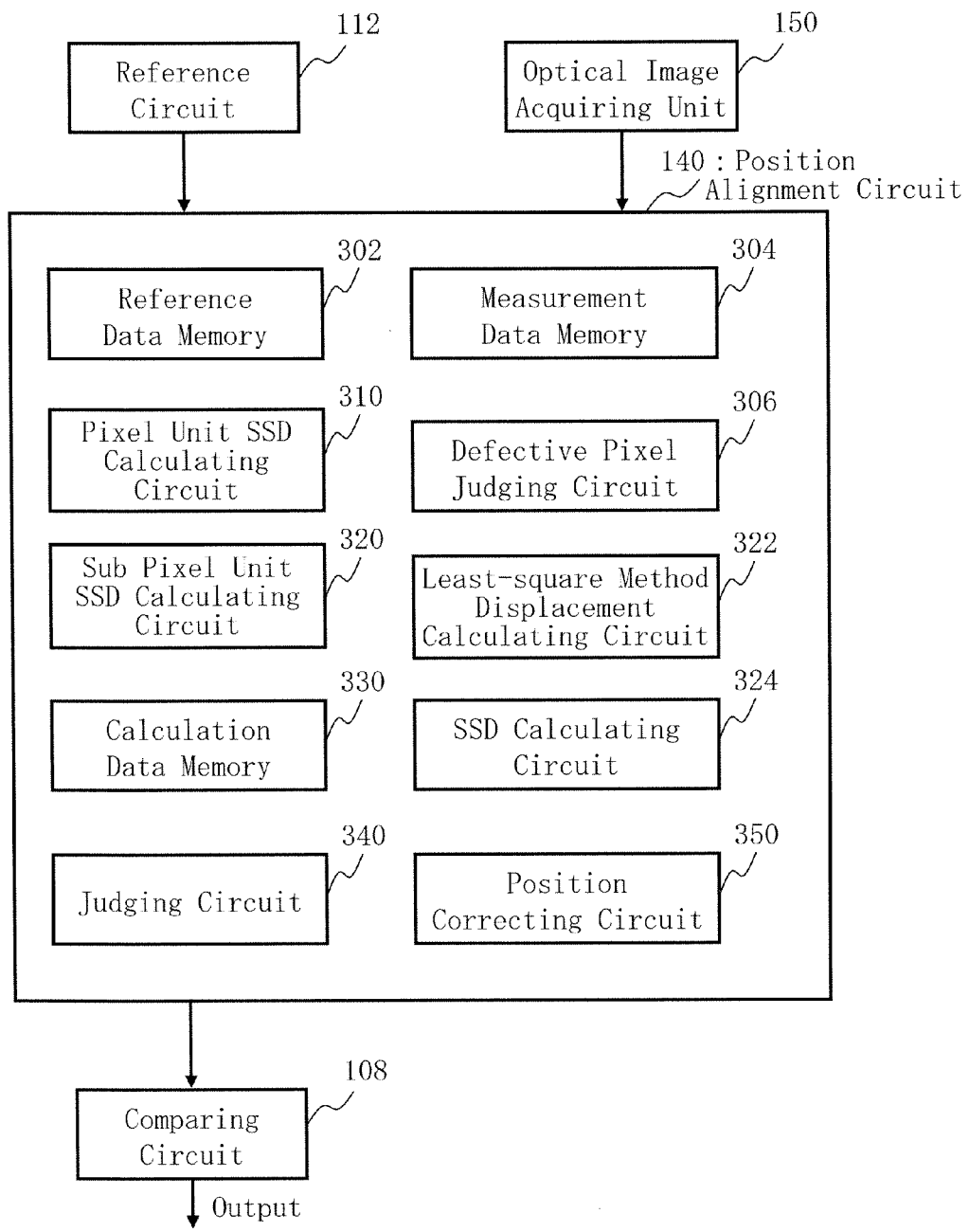
FIG. 13 is a block diagram showing the structure of an alignment circuit described in Embodiment 3.

FIG. 13 is a block diagram showing an example of the structure of the alignment circuit described in Embodiment 3. In the figure, the alignment circuit 140 includes the reference data memory 302, the measurement data memory 304, the defective pixel judging circuit 306, a pixel unit SSD calculating circuit 310, a sub-pixel unit SSD calculating circuit 320, the least-squares method displacement calculating circuit 322, the calculation data memory 330, an SSD (or "Residual Sum of Square (RSS)") calculating circuit 324, a judging circuit 340, and a position correcting circuit 350. The position alignment circuit 140 receives reference data from the reference circuit 112 and measurement data from the optical image acquiring unit 150, performs the alignment of these items of data, and outputs the reference data and the measurement data to the comparing circuit 108. Each of the structure in the defective pixel judging circuit 306 and each of the structure in the least-squares method displacement calculating circuit 322 are the same as those of FIG. 2 or FIG. 10.

Figure 14:
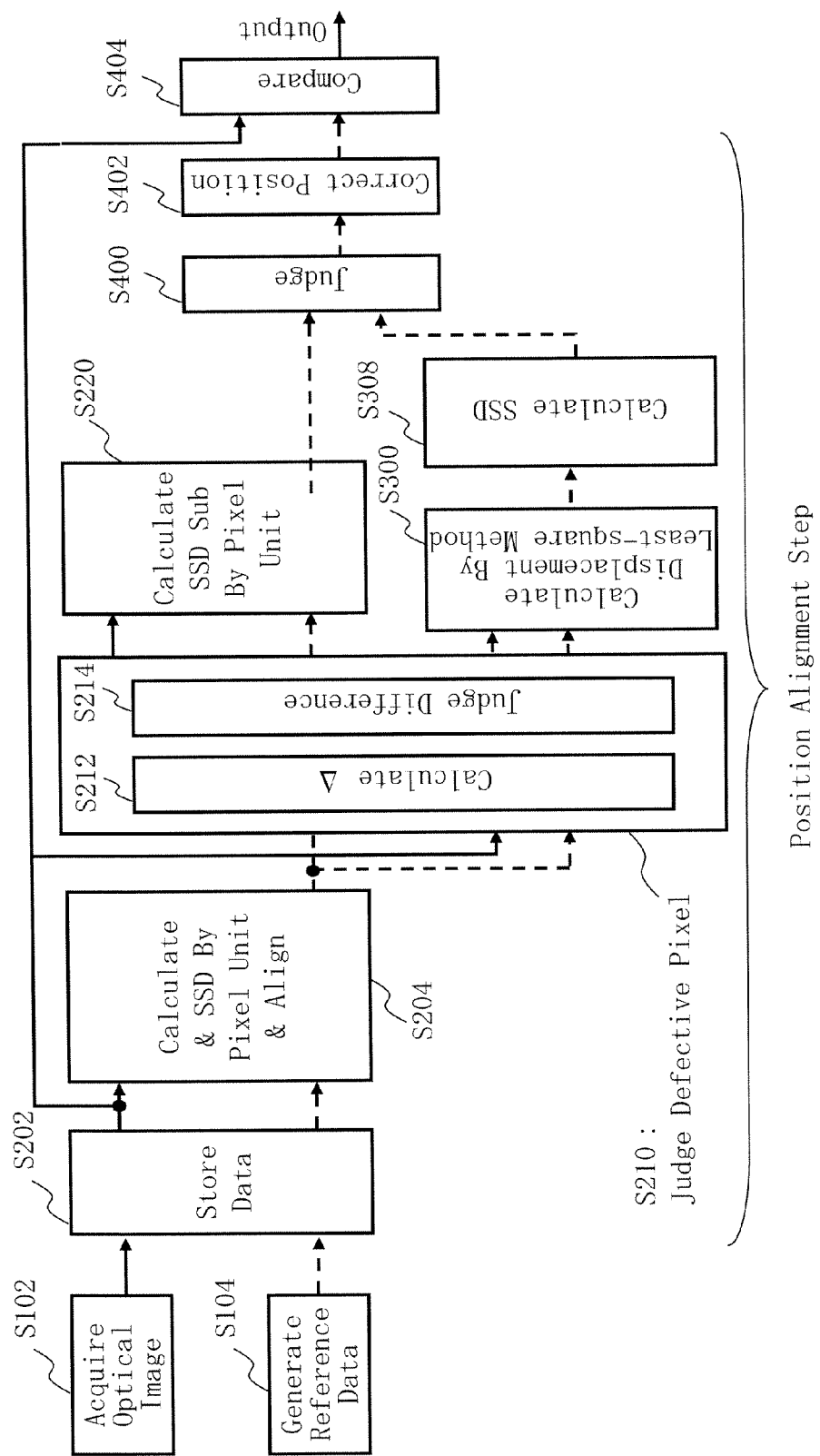
FIG. 14 is a flowchart showing main steps of a target workpiece inspection method described in Embodiment 3.

FIG. 14 is a flowchart showing main steps of a target workpiece inspection method described in Embodiment 3. In the figure, the target workpiece inspection method executes a series of steps including the optical image acquiring step (S102), the reference data generating step (S104), the alignment step, and the comparing step (S404). As the alignment step being one example of the image alignment method, a series of steps including the storing step (S202), a pixel unit SSD calculating step (S204), the defective pixel judging step (S210), a sub-pixel unit SSD calculating step (S220), the least-squares method displacement calculating step (S300), a SSD calculating step (S308), a judging step (S400), and the position correcting step (S402) are executed. In FIG. 14 as well as FIG. 3, solid lines show the flow of measurement data (optical image), and dotted lines show the flow of reference data.

Each of the steps from S102 to S202 is the same as that in Embodiment 1 or Embodiment 2.

In step S204, as the pixel unit SSD calculating step, the pixel unit SSD calculating circuit 310 serving as one example of an SSD calculating unit calculates a displacement amount from a first preliminary alignment position to a position where the SSD between a pixel value of the measurement data and a pixel value of the reference data becomes the minimum, by performing shifting in a pixel unit from the first preliminary alignment position. A position which should be tentatively in accordance in the data coordinate system can be used as the first preliminary alignment position, which is the same as Embodiment 1 or 2.

Figure 15:
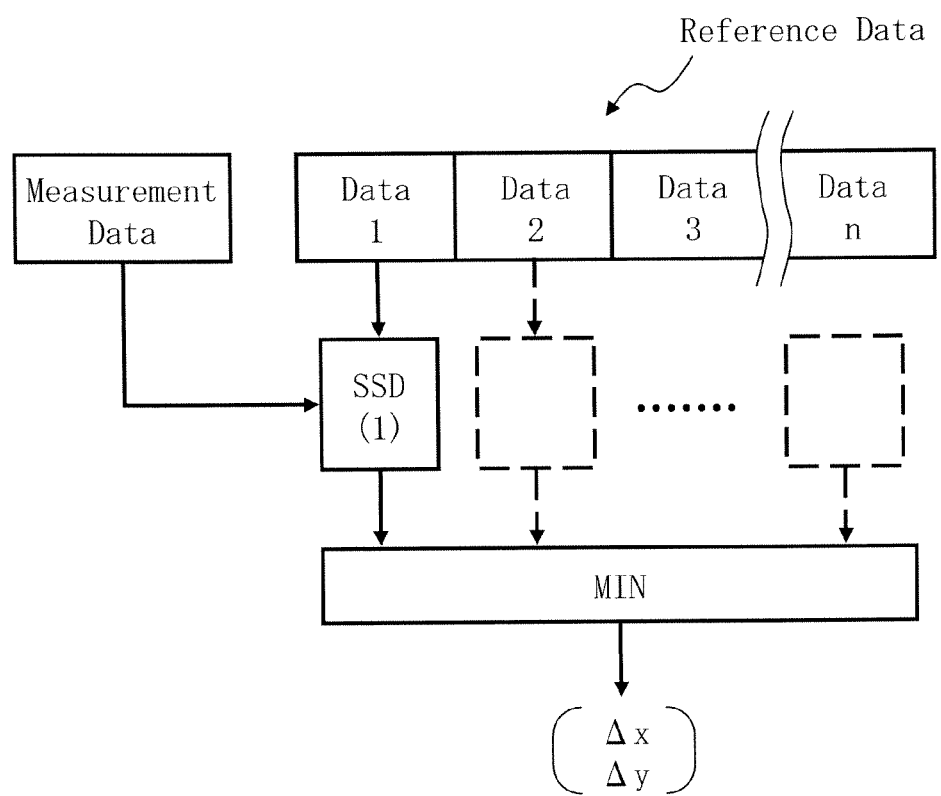
FIG. 15 is a diagram for explaining an SSD calculation method described in Embodiment 3.

FIG. 15 is a diagram for explaining an SSD calculation method described in Embodiment 3. First, the pixel unit SSD calculating circuit 310 reads reference data of an image area of a predetermined size (frame) serving as the unit of comparing process, from the reference data memory 302 on the basis of positional information from the position circuit 107. At this moment, the pixel unit SSD calculating circuit 310 respectively generates images (displaced images), shifted in parallel in units of pixels, with respect to the reference data of such a frame. In FIG. 15, the generated images are shown as data 1, data 2, . . . data n. The measurement data and the reference data in the frame are compared. For example, it is preferable to make an area of 512×512 pixels as one frame. Between each item of plural reference data displaced in units of pixels and the measurement data of the area of the same size read from the measurement data memory 304, the SSD is calculated. The SSD is obtained by summing the squared residual between each pixel value of the reference data and each pixel value of the measurement data. Then, the SSD of each of the plural reference data is calculated, and the minimum value of the SSD is calculated. The measurement data and the reference data are aligned to a position where the minimum value is obtained. In this manner, it is possible to make alignment to the position where the measurement data and the reference data are positioned closest when shifted in parallel in x and y directions in units of pixels. Such a position is made as a second preliminary alignment position, and a detailed alignment is performed hereinafter.

In step S210, as the defective pixel judging step, the defective pixel judging circuit 306 judges a defective pixel using a predetermined threshold value as shown below. Details of each step in the defective pixel judging are the same as those in Embodiment 1.

In step S206, as the sub-pixel image unit SSD calculating step, the sub-pixel unit SSD calculating circuit 320 serving as one example of the SSD calculating unit performs displacing in units of pixels from the second preliminary alignment position between the measurement data and the reference data, which is preliminarily aligned in the pixel unit SSD calculating step, to the position (first position) where the SSD between a pixel value of the measurement data and a pixel value of the reference data is minimized, and calculates the displacement amount (first displacement amount) from the second preliminary alignment position to the first position. At this moment, the calculation is performed while excluding a large defect pixel whose difference is not smaller than the threshold value $\Delta$ in the defective pixel judging step. Therefore, it is possible to prevent excessively aligning the reference data because of being affected by a large defect.

The sub-pixel unit SSD calculating method is the same as the contents explained with reference to FIG. 15. On the basis of the second preliminary alignment position, images (displaced images) shifted in parallel in units of sub-pixels are respectively generated with respect to the reference data of the size of the area to be compared. In FIG. 15, the generated images are shown as data 1, data 2, ... data n. For example, as sub-pixels, ⅛, 1/16, 1/32 and the like of one pixel are made into units. For example, when ⅛ of one pixel is made as the unit of the sub-pixel, the reference data of areas of a predetermined size displaced by ±⅛ pixel, ±2/8 pixel, ±3/8 pixel, ±4/8 pixel, ±5/8 pixel, ±6/8 pixel, and ±7/8 pixel in the X direction and the Y direction, respectively, and the reference data with the displacement amount of 0 are generated. That is, 256 kinds of reference data in a combination of 16 ways in the X direction and 16 ways in the Y direction are generated. Then, the SSD is calculated between the respective reference data and the respective measurement data. The SSD is obtained by summing the squared residual between each pixel value of the reference data and each pixel value of the measurement data. Then, the SSD of each of the plural reference data is calculated, and the minimum value of the SSD is calculated. In this manner, it is possible to obtain the displacement amount to the position where the minimum value is obtained. The data such as the displacement amount which has been set and the calculated SSD are stored in the calculation data memory 330. In this way, it is possible to obtain the displacement amount ($x_0$, $y_0$) for alignment of the measurement data and the reference data to the position where they are positioned closest when shifted in parallel in the X and Y directions in units of sub-pixels.

In step S300, as the least-squares method displacement calculating step, the least-squares method displacement calculating circuit 322 serving as one example of a least-squares method calculating unit calculates a displacement amount (second displacement amount) based on the least-squares method displaced from the above-mentioned second preliminary alignment position between the measurement data and the reference data. The contents of the displacement calculation based on a least-squares method is the same as those in Embodiment 1 or Embodiment 2. That is, the displacement amount etc. is obtained by a displacement calculation based on the least-squares method, using a regular matrix in which each element is calculated while making the element of a large defect pixel be 0 or deleted. In other words, according to the method of Embodiment 1, it is possible to obtain 4(N+4) variables, such as image transmission loss ratios $\epsilon_0$ to $\epsilon_N$, displacement amounts $x_0$, and $y_0$, and a graylevel offset $\delta$. According to the method of Embodiment 2, it is possible to obtain 4(N+4) variables, such as image transmission loss ratios $\epsilon_{0(0)}$ to $\epsilon_{N(3)}$, displacement amounts $x_{0(0)}$, $x_{0(1)}$, $x_{0(2)}$, $x_{0(3)}$, $y_{0(0)}$, $y_{0(1)}$, $y_{0(2)}$, and $y_{0(3)}$, and graylevel offsets $\delta_{(0)}$ to $\delta_{(3)}$. In the case where dividing is performed by weighting as the method of Embodiment 2, the displacement amount ($x_0$, $y_0$) for alignment to the position where the measurement data and the reference data are positioned closest can be obtained by composing. In the methods of Embodiments 1 and 2, if indeterminate solutions exist, the number of the indeterminate solutions are excluded as a matter of course.

In step S308, as the SSD calculating step, the SSD calculating circuit 324 serving as one example of the SSD calculating unit calculates the SSD between a pixel value of the measurement data and a pixel value of the reference data at the position (x-$x_0$, y-$y_0$) (second position) displaced by the displacement amount ($x_0$, $y_0$) calculated by the least-squares method displacement calculating circuit 322 from the above-mentioned preliminary alignment position between the measurement data and the reference data. At this moment, the calculation is performed while excluding a large defect pixel whose difference is not smaller than the threshold value $\Delta$ in the defective pixel judging step. Therefore, it is possible to prevent excessively aligning the reference data because of being affected by a large defect.

In step S400, as the judging step, the judging circuit 340 serving as an example of a judging unit judges which of the SSD at the first position and the SSD at the second position is smaller. That is, the judging circuit 340 judges which of the minimum SSD obtained as the result of the calculation by the sub-pixel unit SSD calculating circuit 320 and the SSD obtained as the result of the calculation by the SSD calculating circuit 324 is smaller. With respect to both the values, since a large defect pixel whose difference is not smaller than the threshold value $\Delta$ in the defective pixel judging step is excluded from both the values in calculation, it is possible to align the targets to be compared, thereby performing a highly precise judgment.

In step S402, as the position correcting step, the position correcting circuit 350 serving as one example of the position correcting unit corrects the alignment position between the measurement data and the reference data to a position where the smaller SSD determined by the judging circuit 340 is obtained. Further, it is also preferable that the position correcting circuit 350 corrects the image graylevel of each pixel of the reference data by use of the image transmission loss ratio $\epsilon$ calculated by the least-squares method displacement calculating circuit 322. For example, not only when the judging circuit 340 adopts the result calculated by the SSD calculating circuit 324, but also when the judging circuit 340 adopts the result calculated by the sub-pixel unit SSD calculating circuit 320, the image graylevel of each pixel of the reference data is preferably corrected by use of the image transmission loss ratio $\epsilon$ calculated by the least-squares method displacement calculating circuit 322.

Herein, the type of patterns suitable for the SSD method or the least-squares method is different. For example, the SSD method is suited for aligning patterns of sparse figure density. On the other hand, the least-squares method is suited for aligning patterns of dense figure density. For this reason, with the configuration as explained in the present Embodiment, the SSD of the least-squares method is compared with the minimum SSD of the SSD in units of sub-pixels, and the correcting method with the smaller SSD between the SSD of the least-squares method and the SSD in units of sub-pixels is adopted, so that better results are expected than those in a case of correction made singly by each of the methods.

More specifically, in the case of an image of a sparse pattern, the calculation by the least-squares method may become unstable, and thus, alignment by the SSD is adopted in that case. A parallel use of the SSD method and the least-squares method makes it possible to stably correct even such a sparse pattern.

By correcting the reference data serving as a reference image or the measurement data serving as an optical image (actual image) by use of such a value, it is possible to make the measurement data and the reference data further closer to each other. As a result, it is possible to prevent a false detection in inspecting defects, and to increase the practical sensitivity. As mentioned above, by simply correcting the displacement between the reference image and the actual image and the image transmission loss, a highly sensitive inspection can be achieved.

Herein, the object to be compared in the judging step is not limited to the SSD, but the sum of the p-th power of a residual wherein p is a positive number may be adopted generally. The SSD corresponds to the case of P=2. In other words, a position correction by the SSD is performed in parallel with the least-squares method, and the sum of the p-th power (p is a positive number) of the residual absolute value of the actual image and the corrected reference image is calculated in the respective cases of the correction by the least-squares method and the correction by the SSD method, both of the values are compared with each other, and a correction method in which the sum of the p-th power of the residual absolute value becomes minimum may be selected. Then, the result of the correcting is output to the comparing circuit 108.

In step S404, as the comparing step, the comparing circuit 108 aligns, by means of the position alignment circuit 140, the measurement data serving as a pattern image to be inspected generated by the sensor circuit 106 on the basis of the transfer image obtained from the photo mask 101, and the reference data serving as an inspection standard pattern image generated by the reference circuit 112, and then takes in both the data. Then, the comparing circuit 108 compares them, namely the taken measurement data and reference data, with each other according to a predetermined algorithm, and judges whether there is a defect or not. The comparing circuit 108 outputs the result of the comparing. Thus, by performing a data comparison through such a highly precise alignment, it is possible to prevent a false detection of a defect and to decrease pseudo defects, thereby performing a highly precise inspection.

Embodiment 4

In Embodiment 3, the case where a sub-pixel unit SSD calculation is performed in parallel with a least-squares method displacement calculation has been explained. In Embodiment 4, the case where the sub-pixel unit SSD calculation is performed in series with the least-squares method displacement calculation will now be explained. The apparatus structure described in Embodiment 4 is the same as that in Embodiment 3. Moreover, each structure in the defective pixel judging circuit 306 and each structure in the least-squares method displacement calculating circuit 322 are the same as those in Embodiment 3, and the same as those of FIG. 2 or FIG. 9.

Figure 16:
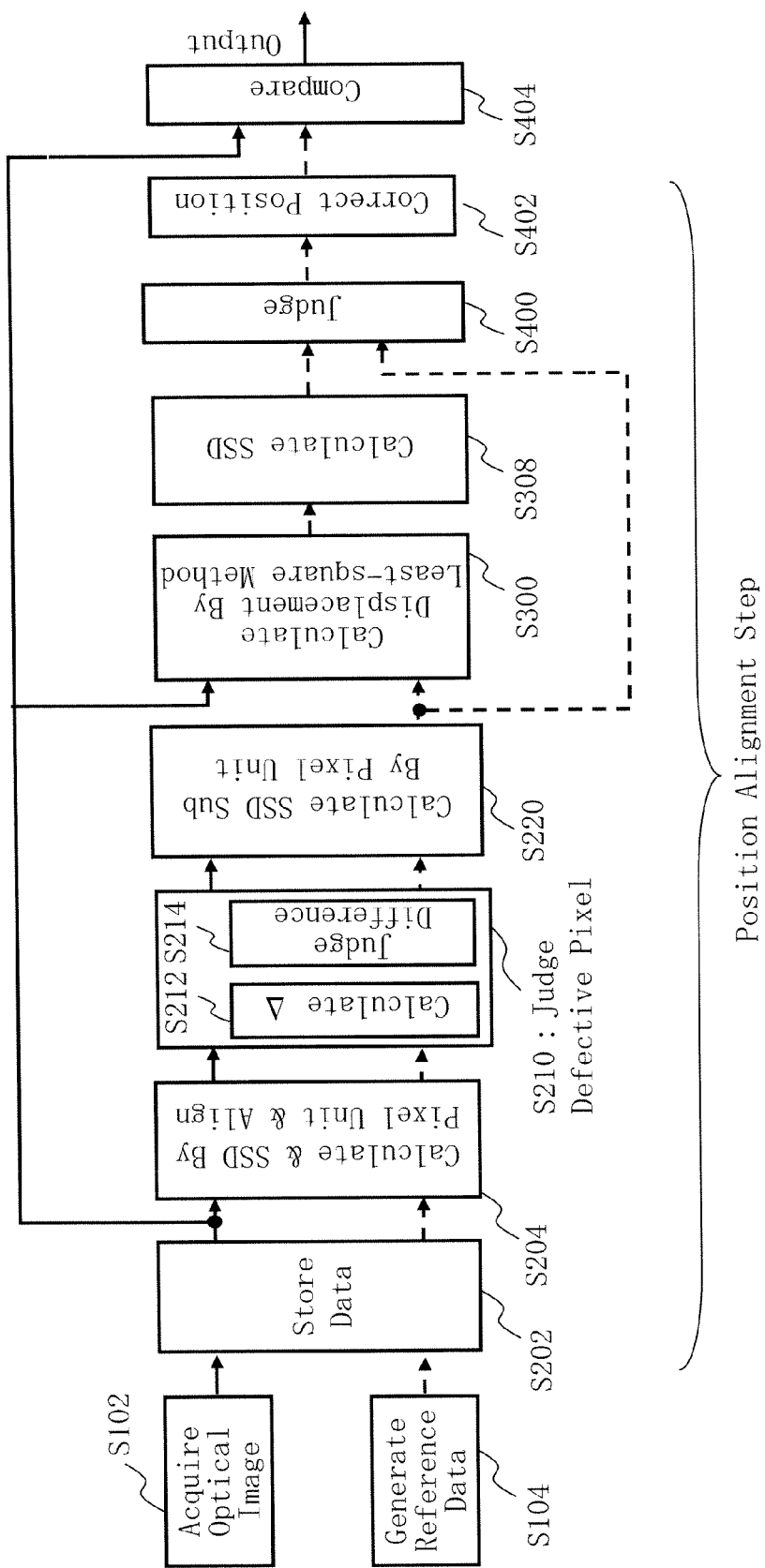
FIG. 16 is a flowchart showing main steps of a target workpiece inspection method described in Embodiment 4.

FIG. 16 is a flowchart showing main steps of the target workpiece inspection method described in Embodiment 4.

In FIG. 14, the sub-pixel unit SSD calculating step (S220) is performed in parallel with a combination of the least-squares method displacement calculating step (S300) and the SSD calculating step (S308). In FIG. 15, after the sub-pixel unit SSD calculating step (S220), the least-squares method displacement calculating step (S300) and the SSD calculating step (S308) are performed, and others are the same as those of FIG. 14. In FIG. 16, as well as FIG. 3, solid lines show the flow of measurement data (optical image), and dotted lines show the flow of reference data.

Each of the steps from S104 to S220 in FIG. 16 is the same as that of Embodiment 3.

In step S300 in FIG. 16, as the least-squares method displacement calculating step, the least-squares method displacement calculating circuit 322 serving as one example of the least-squares method calculating unit calculates a displacement amount (second displacement amount) based on the least-squares method displaced from the first position of the measurement data and the reference data. That is, further alignment is performed for the position (first position) where the minimum SSD obtained as a result of calculating by the sub-pixel unit SSD calculating circuit 320. Thus, by performing further alignment from the position obtained by the sub-pixel unit SSD calculation, highly precise alignment can be performed. The contents of the displacement amount calculation based on the least-squares method are the same as those in Embodiment 1 or 2, that is, the same as those in Embodiment 3.

In step S308 in FIG. 16, as the SSD calculating step, the SSD calculating circuit 324 serving as one example of the SSD calculating unit calculates an SSD between the pixel value of the measurement data and the pixel value of the reference data at the position ($x-x_0$, $y-y_0$) (second position) obtained by displaced by the displacement amount ($x_0$, $y_0$) calculated by the least-squares method displacement calculating circuit 322 from the above-mentioned first position of the measurement data and the reference data.

In step S400 of FIG. 16, as the judging step, the judging circuit 340 serving as one example of the judging unit judges which of the SSD at the first position and the SSD at the second position is smaller. That is, the judgment circuit 340 judges which of the minimum SSD obtained as the result of the calculation by the sub-pixel unit SSD calculating circuit 320 and the SSD obtained as the result of the calculation by the SSD calculating circuit 324 is smaller. The following is the same as Embodiment 3.

As mentioned above, by performing alignment from the position obtained by the sub-pixel unit SSD calculation, it is possible to further enhance the precision of Embodiment 3.

Figure 17:
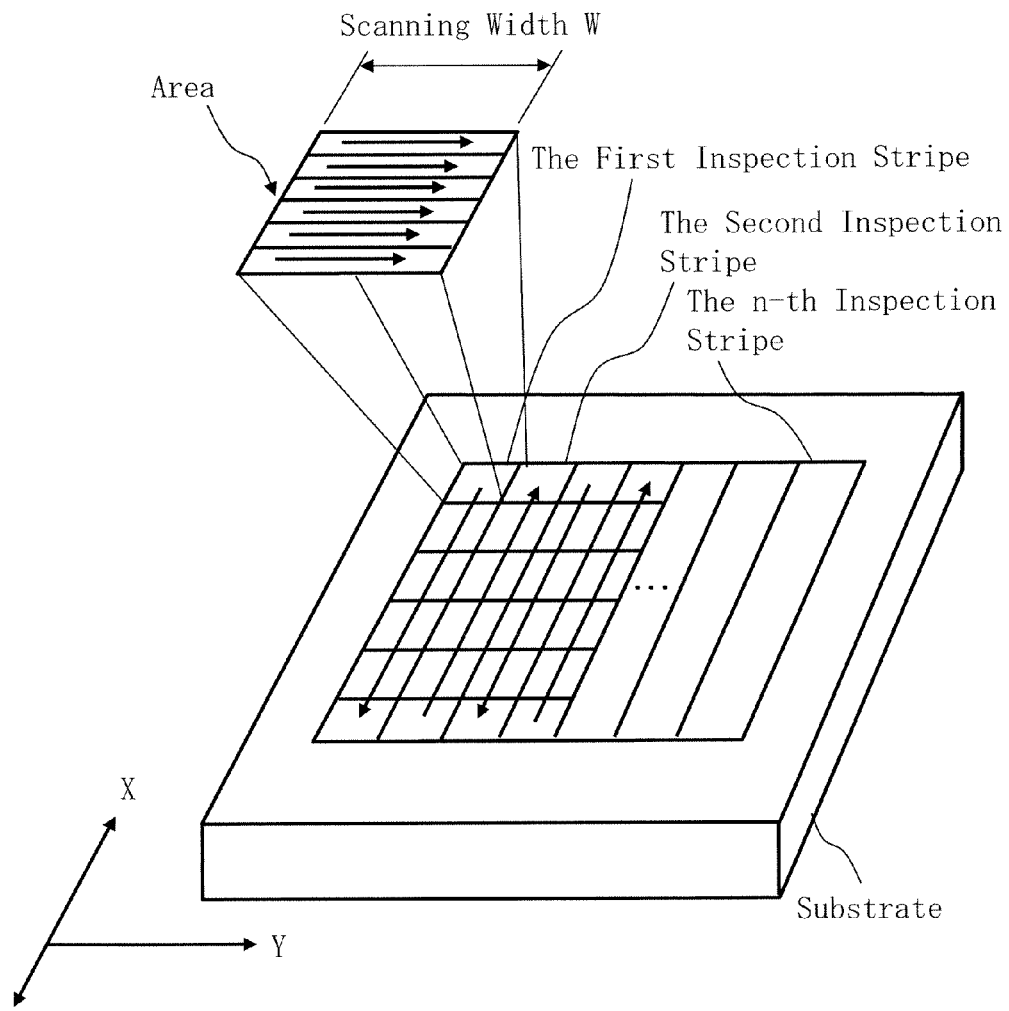
FIG. 17 is a diagram for explaining another method of acquiring an optical image.

In each of the Embodiments mentioned above, with the configuration of FIG. 1, the photodiode array 105 which simultaneously inputs beams corresponding to the number of pixels (for example, 2048 pixels) of the scanning width W is employed, but not limited to it. FIG. 17 is a diagram for explaining another method for acquiring an optical image. As shown in FIG. 17, an alternative method may be used in which, while the XYθ table 102 is transferred at a constant speed in the X direction, a laser scanning optical device (not shown) scans with a laser beam in the Y direction at every time when movement of a predetermined pitch is detected by a laser interferometer, and transmitted light is detected to acquire a two-dimensional image in every area having a predetermined size.

According to each Embodiment described above, it is possible to perform alignment while excluding alignment of a pixel which is not smaller than a predetermined threshold value. As a result, excessive alignment can be prevented, thereby performing highly precise alignment. Consequently, a highly sensitive inspection can be achieved.

What is expressed by "unit", "circuit" or "step" in the above description can be configured by a computer-executable program. They may be executed by a software program or by any combination of software, hardware and/or firmware. Alternatively, they may be configured by hardware. When configured by a program, the program is recordable or storable onto a recording medium, such as a magnetic disk drive, magnetic tape drive, FD or ROM (read-only memory). For example, the table control circuit 114, the reference circuit 112, the comparing circuit 108, the position alignment circuit 140, the respective circuits in the position alignment circuit 140, and the like may be constituted by electric circuits or the like. Alternatively, they may be achieved as software processable by the control computer 110, or achieved by a combination of electric circuits and software.

As mentioned above, Embodiments have been described with reference to the concrete examples. However, the present invention is not limited to these concrete examples. For example, transmitted light is used in Embodiments, but reflected light may also be used, or transmitted light and reflected light may be used simultaneously. The reference image is generated from design data, but alternatively, data of a same pattern photo-captured by a sensor such as a photodiode array may be employed. In other words, it is equally preferable to employ the die to die inspection or the die to database inspection.

Moreover, though apparatus configurations, control methods, etc. which are not directly required in explaining the present invention are not described, a necessary apparatus configuration and a necessary control method can be appropriately selected and used.

Furthermore, all of target workpiece inspection apparatuses, target workpiece inspection methods, image alignment methods, and positional displacement estimating methods which have the elements of the present invention and which can be appropriately changed in design by a person skilled in the art are included in the spirit and scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A target workpiece inspection apparatus comprising:
   an optical image acquiring unit configured to acquire an optical image of a target workpiece to be inspected on which a pattern is formed;
   a reference image generating unit configured to generate a reference image to be compared with the optical image;
   a difference judging unit configured to judge whether an absolute value of difference between a pixel value of the optical image and a pixel value of the reference image in each pixel at a preliminary alignment position between the optical image and the reference image is smaller than a predetermined threshold value;
   a least-squares method displacement calculating unit configured to calculate a displacement amount displaced from the preliminary alignment position, by using a regular matrix for a least-squares method obtained from a result judged by the difference judging unit;
   a position correcting unit configured to correct an alignment position between the optical image and the reference image to a position displaced from the preliminary alignment position by the displacement amount; and
   a comparing unit configured to compare the optical image and the reference image whose alignment position has been corrected.

2. The target workpiece inspection apparatus according to claim 1, wherein the regular matrix is calculated by deleting a product-sum term corresponding to a pixel whose absolute value of the difference is equal to or larger than the predetermined threshold value, from a product-sum calculation for obtaining all elements of the regular matrix.

3. The target workpiece inspection apparatus according to claim 2, wherein the predetermined threshold value includes an absolute value of a maximum of an image transmission loss ratio generated from apparatus features, an absolute value of a maximum of a displacement amount in X direction generated from the apparatus features, and an absolute value of a maximum of a displacement amount in Y direction generated from the apparatus features, as parameters.

4. The target workpiece inspection apparatus according to claim 3, wherein the predetermined threshold value is obtained by at least adding a value calculated by multiplying the absolute value of the maximum of the image transmission loss ratio by the pixel value of the reference image, a value calculated by multiplying the absolute value of the maximum of the displacement amount in the X direction by an absolute value of a first differential value obtained by space differentiating the reference image in the X direction, and a value calculated by multiplying the absolute value of the maximum of the displacement amount in the Y direction by an absolute value of a second differential value obtained by space differentiating the reference image in the Y direction.

5. The target workpiece inspection apparatus according to claim 1, wherein the least-squares method displacement calculating unit divides the reference image by weighting, and calculates the displacement amount for each of divided areas.

6. A target workpiece inspection apparatus comprising:
   an optical image acquiring unit configured to acquire an optical image of a target workpiece to be inspected on which a pattern is formed;
   a reference image generating unit configured to generate a reference image to be compared with the optical image;
   a difference judging unit configured to judge whether an absolute value of difference between a pixel value of the optical image and a pixel value of the reference image in each pixel at a preliminary alignment position between the optical image and the reference image is smaller than a predetermined threshold value;
   a first SSD (Sum of Squared Difference) calculating unit configured to calculate a first displacement amount from the preliminary alignment position between the optical image and the reference image to a first position where an SSD between the pixel value of the optical image and the pixel value of the reference image is minimized;
   a least-squares method displacement calculating unit configured to calculate a second displacement amount displaced from the preliminary alignment position, by using a regular matrix for a least-squares method obtained from a result determined by the difference judging unit;

a second SSD calculating unit configured to calculate an SSD between the pixel value of the optical image and the pixel value of the reference image at a second position displaced from the preliminary alignment position by the second displacement amount;

an SSD judging unit configured to judge which of the SSD at the first position and the SSD at the second position is smaller;

a position correcting unit to correct an alignment position between the optical image and the reference image to a position where a smaller SSD as a result determined by the SSD judging unit is obtained; and a comparing unit configured to compare the optical image and the reference image whose alignment position has been corrected.

7. The target workpiece inspection apparatus according to claim 6, wherein the regular matrix is calculated by deleting a product-sum term corresponding to a pixel whose absolute value of the difference is equal to or larger than the predetermined threshold value, from a product-sum calculation for obtaining all elements of the regular matrix.

8. The target workpiece inspection apparatus according to claim 7, wherein the predetermined threshold value includes an absolute value of a maximum of an image transmission loss ratio generated from apparatus features, an absolute value of a maximum of a displacement amount in X direction generated from the apparatus features, and an absolute value of a maximum of a displacement amount in Y direction generated from the apparatus features, as parameters.

9. The target workpiece inspection apparatus according to claim 8, wherein the predetermined threshold value is obtained by at least adding a value calculated by multiplying the absolute value of the maximum of the image transmission loss ratio by the pixel value of the reference image, a value calculated by multiplying the absolute value of the maximum of the displacement amount in the X direction by an absolute value of a first differential value obtained by space differentiating the reference image in the X direction, and a value calculated by multiplying the absolute value of the maximum of the displacement amount in the Y direction by an absolute value of a second differential value obtained by space differentiating the reference image in the Y direction.

10. Target workpiece inspection apparatus according to claim 6, wherein the first SSD calculating unit calculates the first displacement amount by performing displacing in units of subpixels to a position where the SSD is minimized.

11. The target workpiece inspection apparatus according to claim 6, wherein the least-squares method displacement calculating unit divides the reference image by weighting, and calculates the displacement amount for each of divided areas.

12. A target workpiece inspection apparatus comprising:

an optical image acquiring unit configured to acquire an optical image of a target workpiece to be inspected on which a pattern is formed;

a reference image generating unit configured to generate a reference image to be compared with the optical image;

a difference judging unit configured to judge whether an absolute value of difference between a pixel value of the optical image and a pixel value of the reference image in each pixel at a preliminary alignment position between the optical image and the reference image is smaller than a predetermined threshold value;

a first SSD (Sum of Squared Difference) calculating unit configured to calculate a first displacement amount from the preliminary alignment position between the optical image and the reference image to a first position where an SSD between the pixel value of the optical image and the pixel value of the reference image is minimized;

a least-squares method displacement calculating unit configured to calculate a second displacement amount displaced from the first position, by using a regular matrix for a least-squares method obtained from a result determined by the difference judging unit;

a second SSD calculating unit configured to calculate an SSD between the pixel value of the optical image and the pixel value of the reference image at a second position displaced from the first position by the second displacement amount;

an SSD judging unit configured to judge which of the SSD at the first position and the SSD at the second position is smaller;

a position correcting unit configured to correct an alignment position between the optical image and the reference image to a position where a smaller SSD as a result determined by the SSD judging unit is obtained; and a comparing unit configured to compare the optical image and the reference image whose alignment position has been corrected.

13. The target workpiece inspection apparatus according to claim 12, wherein the regular matrix is calculated by deleting a product-sum term corresponding to a pixel whose absolute value of the difference is equal to or larger than the predetermined threshold value, from a product-sum calculation for obtaining all elements of the regular matrix.

14. The target workpiece inspection apparatus according to claim 13, wherein the predetermined threshold value includes an absolute value of a maximum of an image transmission loss ratio generated from apparatus features, an absolute value of a maximum of a displacement amount in X direction generated from the apparatus features, and an absolute value of a maximum of a displacement amount in Y direction generated from the apparatus features, as parameters.

15. The target workpiece inspection apparatus according to claim 14, wherein the predetermined threshold value is obtained by at least adding a value calculated by multiplying the absolute value of the maximum of the image transmission loss ratio by the pixel value of the reference image, a value calculated by multiplying the absolute value of the maximum of the displacement amount in the X direction by an absolute value of a first differential value obtained by space differentiating the reference image in the X direction, and a value calculated by multiplying the absolute value of the maximum of the displacement amount in the Y direction by an absolute value of a second differential value obtained by space differentiating the reference image in the Y direction.

16. The target workpiece inspection apparatus according to claim 12, wherein the first SSD calculating unit calculates the first displacement amount by performing displacing in units of subpixels to a position where the SSD is minimized.

17. The target workpiece inspection apparatus according to claim 12, wherein the least-squares method displacement calculating unit divides the reference image by weighting, and calculates the displacement amount for each of divided areas.

18. An image alignment method for aligning an optical image and a reference image for use in a comparing inspection of a target workpiece to be inspected on which a pattern is formed, the method comprising:

judging whether an absolute value of difference between a pixel value of the optical image and a pixel value of the reference image in each pixel at a preliminary alignment position between the optical image and the reference image is smaller than a predetermined threshold value;

calculating a first displacement amount from the preliminary alignment position between the optical image and the reference image to a first position where an SSD (Sum of Squared Difference) between the pixel value of the optical image and the pixel value of the reference image is minimized;

calculating a second displacement amount displaced from the first position, by using a regular matrix for a least-squares method obtained from a result of the judging of difference;

calculating an SSD between the pixel value of the optical image and the pixel value of the reference image at a second position displaced from the first position by the second displacement amount;

judging which of the SSD at the first position and the SSD at the second position is smaller; and correcting an alignment position between the optical image and the reference image to a position where a smaller SSD as a result of the judging is obtained, to output a result of the correcting.

19. A computer-readable recording medium with a program recorded thereon to be executed by a computer comprising:

storing process for storing an optical image and a reference image for use in a comparing inspection of a target workpiece to be inspected on which a pattern is formed, in a storage device;

difference judging process for judging whether an absolute value of difference between a pixel value of the optical image and a pixel value of the reference image in each pixel at a preliminary alignment position between the optical image and the reference image is smaller than a predetermined threshold value by reading the optical image and the reference image from the storage device; and least-squares method displacement calculating process for calculating a displacement amount based on a least-squares method by using a regular matrix for the least-squares method obtained from a result of the difference judging process, to output the displacement amount.

* * * * *